US012616599B2

(12) United States Patent
Volz

(10) Patent No.: US 12,616,599 B2
(45) Date of Patent: May 5, 2026

(54) SYSTEMS AND METHODS FOR MAINTAINING PATIENT POSITION

(71) Applicant: Volz Surgical Consulting Inc., Dakota Dunes, SD (US)

(72) Inventor: Lawrence T. Volz, Dakota Dunes, SD (US)

(73) Assignee: Volz Surgical Consulting Inc., Dakota Dunes, SD (US)

( * ) Notice: Subject to any disclaimer, the term of this patent is extended or adjusted under 35 U.S.C. 154(b) by 100 days.

(21) Appl. No.: 18/649,505

(22) Filed: Apr. 29, 2024

(65) Prior Publication Data

US 2024/0366413 A1 Nov. 7, 2024

Related U.S. Application Data

(60) Provisional application No. 63/463,105, filed on May 1, 2023.

(51) Int. Cl.
 *A61F 5/37* (2006.01)
 *A61G 13/12* (2006.01)

(52) U.S. Cl.
 CPC ........ *A61F 5/3769* (2013.01); *A61G 13/1235* (2013.01); *A61G 13/124* (2013.01); *A61G 13/1245* (2013.01); *A61G 13/125* (2013.01)

(58) Field of Classification Search
 CPC . A61F 5/3769; A61G 13/1235; A61G 13/124; A61G 13/1245; A61G 13/125; A61G 1/044; A61G 1/048; A61G 13/122; A61G 13/126; A61G 13/1285
 USPC ....................................................... 600/415
 See application file for complete search history.

(56) References Cited

U.S. PATENT DOCUMENTS

| | | | |
|---|---|---|---|
| 2,245,293 A | | 6/1941 | Ogburn |
| 2,510,198 A | | 6/1950 | Tesmer |
| 3,096,962 A | | 7/1963 | Meijs |
| 3,168,274 A | | 2/1965 | Street |
| 3,858,578 A | | 1/1975 | Milo |
| 4,239,036 A | * | 12/1980 | Krieger .................. A61B 17/02 |
| | | | 600/206 |
| 4,303,116 A | * | 12/1981 | Holzwarth .............. B60C 27/16 |
| | | | 152/224 |
| 4,473,912 A | | 10/1984 | Scheidel et al. |
| 4,526,165 A | * | 7/1985 | Mielnik, Jr. ........... A61G 13/12 |
| | | | 128/882 |
| 4,729,138 A | | 3/1988 | Heyman et al. |
| 4,766,892 A | * | 8/1988 | Kreitman ........... A61G 13/0063 |
| | | | 5/624 |

(Continued)

FOREIGN PATENT DOCUMENTS

EP 3804685 4/2021

OTHER PUBLICATIONS

International Search Report and Written Opinion in International Appln. No. PCT/US/2024/026818, mailed on Sep. 3, 2024, 16 pages.

(Continued)

*Primary Examiner* — Justin C Mikowski
*Assistant Examiner* — George Samuel Gines
(74) *Attorney, Agent, or Firm* — Fish & Richardson P.C.

(57) ABSTRACT

Some systems, devices and methods detailed herein provide adjustable restraint device maintaining a selected position of a person relative to a support structure, for example, to maintain a safe and customizable patient position during a surgical procedure or during medical transport.

14 Claims, 13 Drawing Sheets

(56) References Cited

U.S. PATENT DOCUMENTS

| 5,348,259 | A | | 9/1994 | Blanco et al. | |
|---|---|---|---|---|---|
| 5,547,463 | A | * | 8/1996 | Hinchliffe | A61B 90/00 |
| | | | | | 600/102 |
| 5,738,675 | A | * | 4/1998 | Botimer | A61F 5/3769 |
| | | | | | 5/624 |
| 7,730,565 | B1 | | 6/2010 | Masson | |
| 8,539,621 | B2 | * | 9/2013 | West | A61G 13/124 |
| | | | | | 5/628 |
| 8,870,141 | B2 | | 10/2014 | Abri et al. | |
| 9,615,987 | B2 | | 4/2017 | Kettle et al. | |
| 11,079,807 | B1 | | 8/2021 | Robinson et al. | |
| 11,638,670 | B1 | | 5/2023 | Volz et al. | |
| 2001/0044967 | A1 | | 11/2001 | Gasper | |
| 2004/0249367 | A1 | * | 12/2004 | Saadat | A61B 1/2736 |
| | | | | | 600/101 |
| 2011/0038064 | A1 | | 2/2011 | Xhunga | |
| 2016/0120726 | A1 | | 5/2016 | Moriarty et al. | |
| 2020/0000623 | A1 | | 1/2020 | Allen | |
| 2023/0381043 | A1 | | 11/2023 | Volz et al. | |

OTHER PUBLICATIONS

International Search Report and Written Opinion in International Appln. No. PCT/US2023/022676, mailed on Sep. 4, 2023, 11 pages.
universalmedicalinc.com [online], "Deluxe Arthroscopic Legholder System," 1983, retrieved on Jul. 12, 2022, retrieved from URL<https://www.universalmedicalinc.com/deluxe-arthroscopic-legholder-system.html>, 7 pages.

* cited by examiner

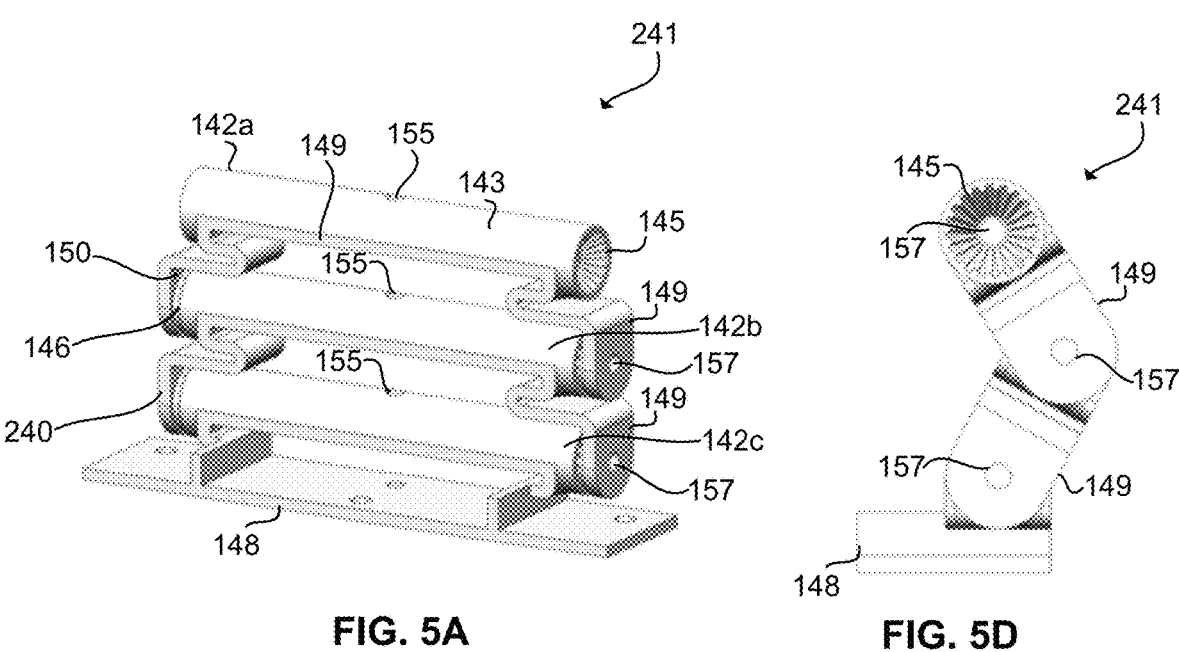
FIG. 5A
FIG. 5D
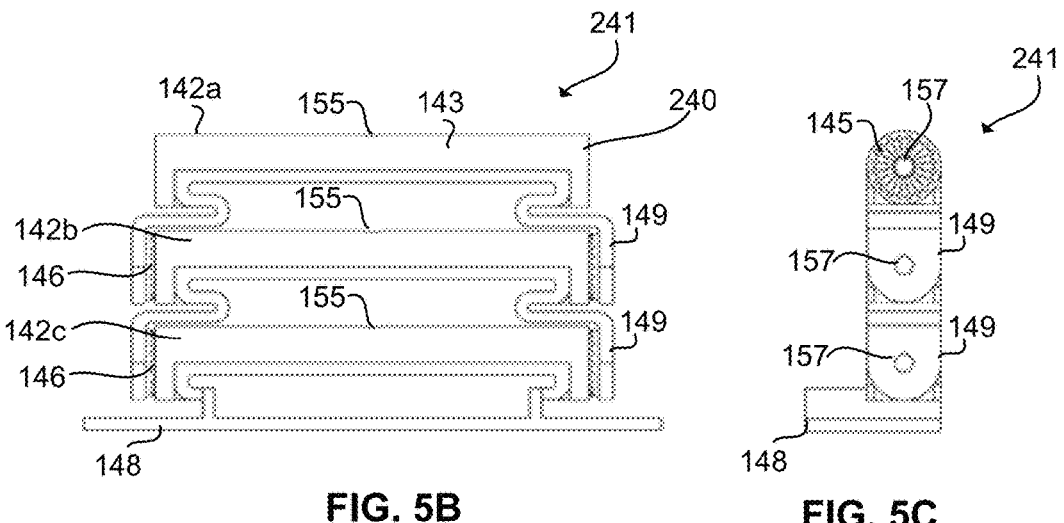
FIG. 5B
FIG. 5C

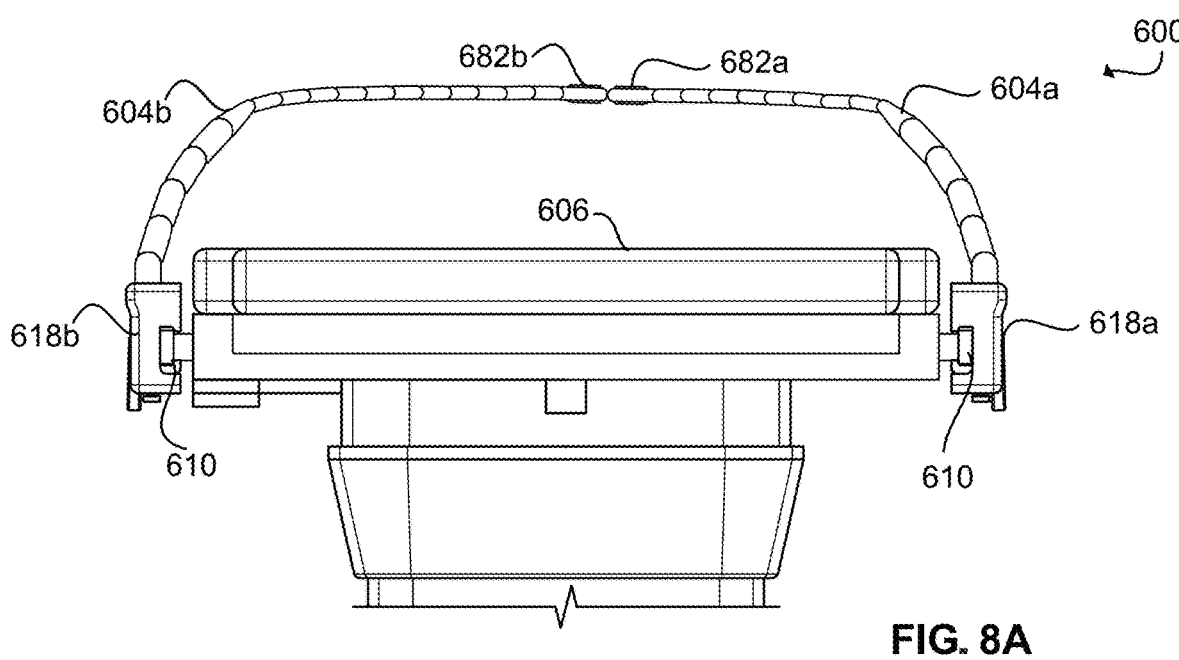
FIG. 8A
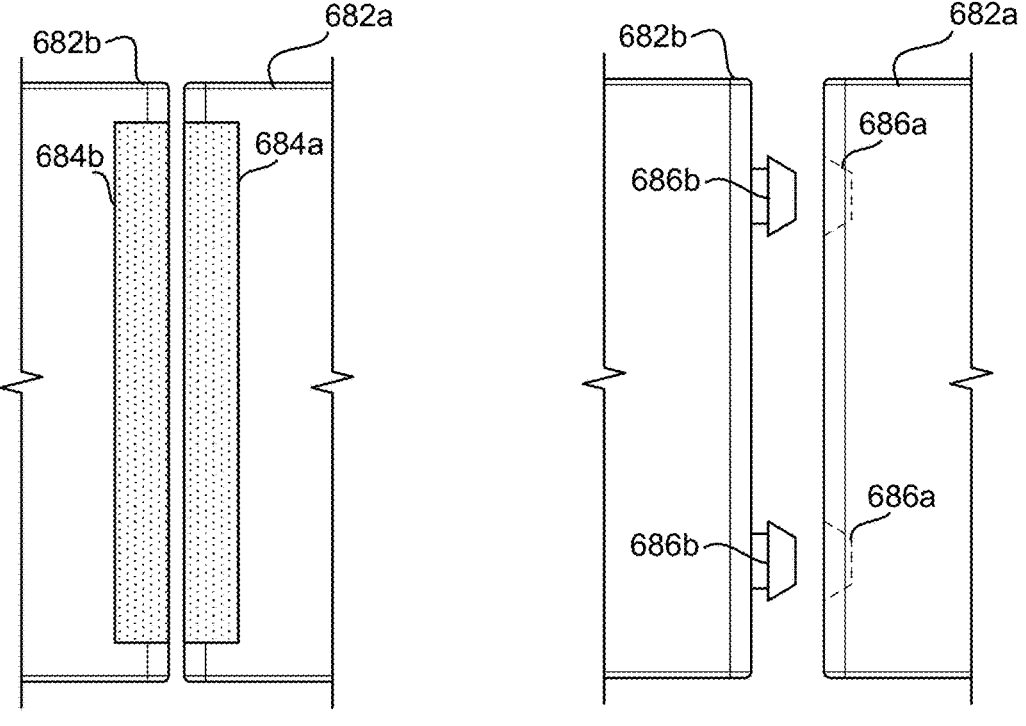
FIG. 8B                     FIG. 8C

SYSTEMS AND METHODS FOR MAINTAINING PATIENT POSITION

CROSS-REFERENCE TO RELATED APPLICATIONS

This application claims priority to U.S. Application No. 63/463,105, filed on May 1, 2023. The disclosure of the prior application is considered part of the disclosure of this application and is incorporated in it's entirety into this application.

TECHNICAL FIELD

This disclosure describes systems, devices, and methods for releasably and safely retaining a subject, such as a patient during surgical procedures or during transport to a medical site. Particular examples described herein provide improved positioning and releasable restraint of one or more limbs of a patient in a customizable and safe position while the patient is sedated during a surgical procedure.

BACKGROUND

Maintaining a consistent and safe position of a patient during a surgical procedure facilitates improved surgical outcomes and reduces the likelihood of inadvertent limb movement and consequences thereof, such as paresthesia or ischemia in a limb that inadvertently shifted positions during the course of a surgery. For example, in some circumstances when a patient can be subjected to anesthesia during a surgical procedure, the patient may not be able to control or position themselves or otherwise alert the medical practitioner of discomfort or paresthesia in a limb. Medical practitioners have employed a number of techniques to control the position of the patient during a medical procedure. For example, some medical staff may utilize folding or cushioning techniques of the sheets on the operating table to hold the patient in position. These techniques can include wrapping a sheet around a patient's limb and into a cushion of the surgical table to hold the patient's limb in position during the procedure. Such a technique can be ineffective at maintaining a consistent and safe position of the patient throughout a procedure because the sheets can loosen in some areas, allowing a limb of the patient to move from the originally selected position. Additionally, in some circumstances involving an obese or oversized patient that occupies areas larger than the surgical table, such conventional techniques may fail to safely retain the patient's limbs in a consistent and safe manner throughout the duration of the medical procedure.

SUMMARY

This disclosure describes systems, devices, and methods for maintaining a selected position of a person relative to a support structure, for example, to achieve a safe and customizable patient position during a surgical procedure or during medical transport of a patient. In particular implementations, the systems, devices, and methods described herein can include at least one adjustable restraint device that achieves improved adjustability for releasably capturing of one or more portions of a patient in a safe position relative to a surgical operating table or medical transport device. In some examples detailed below, the adjustable restraint device can include a series of movable links that provides convenient adjustability to a user-selected position and shape, and in response to a user adjusting an actuator of the adjustable restraint device, the links are locked in the user-selected position/shape (e.g., via engagement of beveled end connectors of the links mechanically mating with one another).

Among other benefits, some systems and methods described herein can advantageously provide a more efficient and customizable approach to maintain any of a wide variety of patient sizes in a selected position a surgical operating table or medical transport device. For example, in particular embodiments, the adjustable restraint devices can be releasably lockable at a user-selected position along the surgical table and/or surgical arm boards and can be conveniently manipulated to a curved or other user-selected configuration (e.g., to engage with a patient's limb) before being releasably locked into that particular user-selected configuration. Additionally, some embodiments described in more detail below can achieve a removable, reusable solution that provides added comfort to a patient engaged with the adjustable restraint device while also achieving efficient disposable of particular components and reuse of other more complex components. And, in a number of optional implementations, the adjustable restraint device can employ a set of links having improved end connectors that provide rapid transition from an unlocked state (in which the adjustable restraint device is readily adjusted to a user-selected position and shape) to a lock state (in which the adjacent links are mechanically locked together) with an increased locking strength and torque resistance.

Some embodiments described herein include, a flexible cuff system for releasably maintaining a position of a patient. The flexible cuff system includes a flexible cuff body adjustable from a first orientation to a user-selected orientation to retain a limb in a selected position relative to a medical support substrate, the flexible cuff body including a series of links that are adjustably connected together via a series of first end connectors of each link body configured to connect to a series of second end connectors of a series of brackets and one or more cables; and a handle body connected to a base portion of the flexible cuff body, the handle body including a handle that is movable between a locked position and an unlocked position, and the handle body defining a mating interface surface that to slidably engage the medical support substrate; where, responsive to the handle being moved to the unlocked position, the flexible cuff body is adjustable from the first orientation to the user-selected orientation to extend around the limb, and where, responsive to the handle being moved to the locked position while the flexible cuff body is in the user-selected orientation, the flexible cuff body is locked in the user-selected orientation by compressing the first end connectors and second end connectors together to retain the limb in the selected position relative to the medical support substrate.

Such a system can include one or more of the following optional features. The flexible cuff system where the one or more cables includes a longitudinal cable that extends from the handle body through the series of links of the flexible cuff body that are adjustably connected together and movable to a linked position relative to one another. Each link may include a transverse cable that connects to the longitudinal cable. The handle is connected to the longitudinal cable, and responsive to the handle being moved to the locked position, the handle applies tension to the longitudinal cable to fix the series of links in the linked position relative to one another. The medical support substrate is a surgical table, and the mating interface surface of the handle body configured to slidably engage with a rail of the surgical table. The medical support substrate is an arm bar extension of a surgical table, and the mating interface surface of the handle body configured to slidably engage with the arm bar extension of a surgical table. The flexible cuff system the flexible cuff body may include a protective outer sleeve removably positioned over the series of links of the flexible cuff body. The series of first end connectors form a beveled spline receiver and the series of second end connectors form a beveled spline. Responsive to the handle being moved to the unlocked position, the series of links are pivotable with respect to each other to adjust an overall shape of the series of links. The flexible cuff body extends away from the handle body toward a free end of the flexible cuff body, and the free end of the flexible cuff body includes a fastener configured to connect to a second flexible cuff body.

Some embodiments described herein include a system. The system can include a surgical table including one or more rails that extend along one or more sides of the surgical table; a plurality of adjustable limb restraints releasably lockable at selectable positions along the one or more rails of the surgical table, each of the adjustable limb restraints including: a flexible cuff body adjustable from a first orientation to a user-selected orientation to retain a limb in a user-selected position relative to the surgical table, the flexible cuff body including a series of links that are adjustably connected together via a series of first end connectors of each link body configured to connect to a series of second end connectors of a series of brackets and one or more cables; and a handle body connected to a base of the flexible cuff body and including a handle movable between a locked position and an unlocked position, and the handle body defining a mating interface surface to slidably engage at least one of the one or more rails. The system also includes where, responsive to the handle being moved to the unlocked position, the flexible cuff body is adjustable from the first orientation to the user-selected orientation to extend around the limb; and where, responsive to the handle being moved to the locked position while the flexible cuff body is in the user-selected orientation, the flexible cuff body is locked in the user-selected orientation by compressing the first end connectors and second end connectors together to retain the limb in the selected position relative to the surgical table.

Such a system can include one or more of the following optional features. The system where the flexible cuff body includes a longitudinal cable that extends from the handle body through the series of links of the flexible cuff body that are adjustably connected together and movable to a linked position relative to one another. Responsive to the handle being moved to the unlocked position, the series of links are movable with respect to each other to adjust the flexible cuff body to the user-selected orientation shaped to extend around the limb. Responsive to the handle being moved to the locked position, the series of links are mechanically fixed relative to each other to releasably lock the flexible cuff body in the user-selected orientation. Responsive to the handle being moved to the unlocked position, the series of links are pivotable with respect to each other to adjust an overall shape of the flexible cuff body. Each of the plurality of adjustable limb restraints operate independently from one another Some embodiments include a method of maintaining a position of a patient. The method can include releasably locking a handle body of an adjustable limb restraint to a rail of an operating table at a selected location relative to a limb of a patient on the operating table; adjusting a flexible cuff body of the adjustable limb restraint to a selected shape to engage with the limb of the patient, and adjusting an actuator on the handle body of the adjustable limb restraint to releasably lock the flexible cuff body in the selected shape by compressing a series of first end connectors and a series of second end connectors of the flexible cuff body together.

Some embodiments of the method can include one or more of the following optional features. The method where said adjusting the flexible cuff body may include pivoting a series of links of the flexible cuff body that are adjustably connected to each other and arranged within a padded sleeve of the flexible cuff body. In response to said adjusting the actuator on the handle body, a series of links of the flexible cuff body are mechanically fixed relative to each other to releasably lock the flexible cuff body in the selected shape. The limb of the patient is an arm, leg, or torso of the patient.

Some embodiments described herein include a system. The system can include a surgical arm board including: a bracket having an interface surface that is configured to connect to one or more rails of a surgical table; a rail assembly releasably connected to the surgical arm board, the rail assembly includes a rail assembly bracket and one or more rails that extend along one or more sides of the surgical arm board.

Particular implementations can, in certain instances, realize one or more of the following advantages. The systems, devices, and methods described herein provide a more secure and consistent approach to holding patients and patient limbs in position on a surgical table or medical transport device that reduces the likelihood that a patient or a patient limb may move out of the desirable position and maintains the original position of the patient or patient limb during the procedure or transport. Additionally, the presently described systems, devices, and methods offer a removable, reusable solution that is advantageously adjustable to capture patients and portions of patients of various sizes and is readily adjustable to engage with different sizes and shapes of patients or patient limbs.

The details of one or more implementations are set forth in the accompanying drawings and the description below. Other features, objects, and advantages will be apparent from the description and drawings, and from the claims.

DESCRIPTION OF DRAWINGS

FIG. 5A shows a perspective view of a portion of the adjustable limb restraint of FIGS. 2A-B, with some links removed from view.

FIG. 5B shows a front view of the adjustable limb restraint of FIG. 5A.

FIG. 5C shows a side view of the adjustable limb restraint of FIG. 5A.

FIG. 5D shows a side view of the adjustable limb restraint of FIG. 5A in another position.

FIG. 8A shows an end view of another example system for positioning a patient using adjustable limb restraints, in accordance with some embodiments of this disclosure.

FIG. 8B shows a top view of an example section of an adjustable limb restraint of the system of FIG. 6A.

FIG. 8C shows a top view of another example section of an adjustable limb restraint of the system of FIG. 8A.

Like reference symbols in the various drawings indicate like elements.

DETAILED DESCRIPTION

Figure 1:
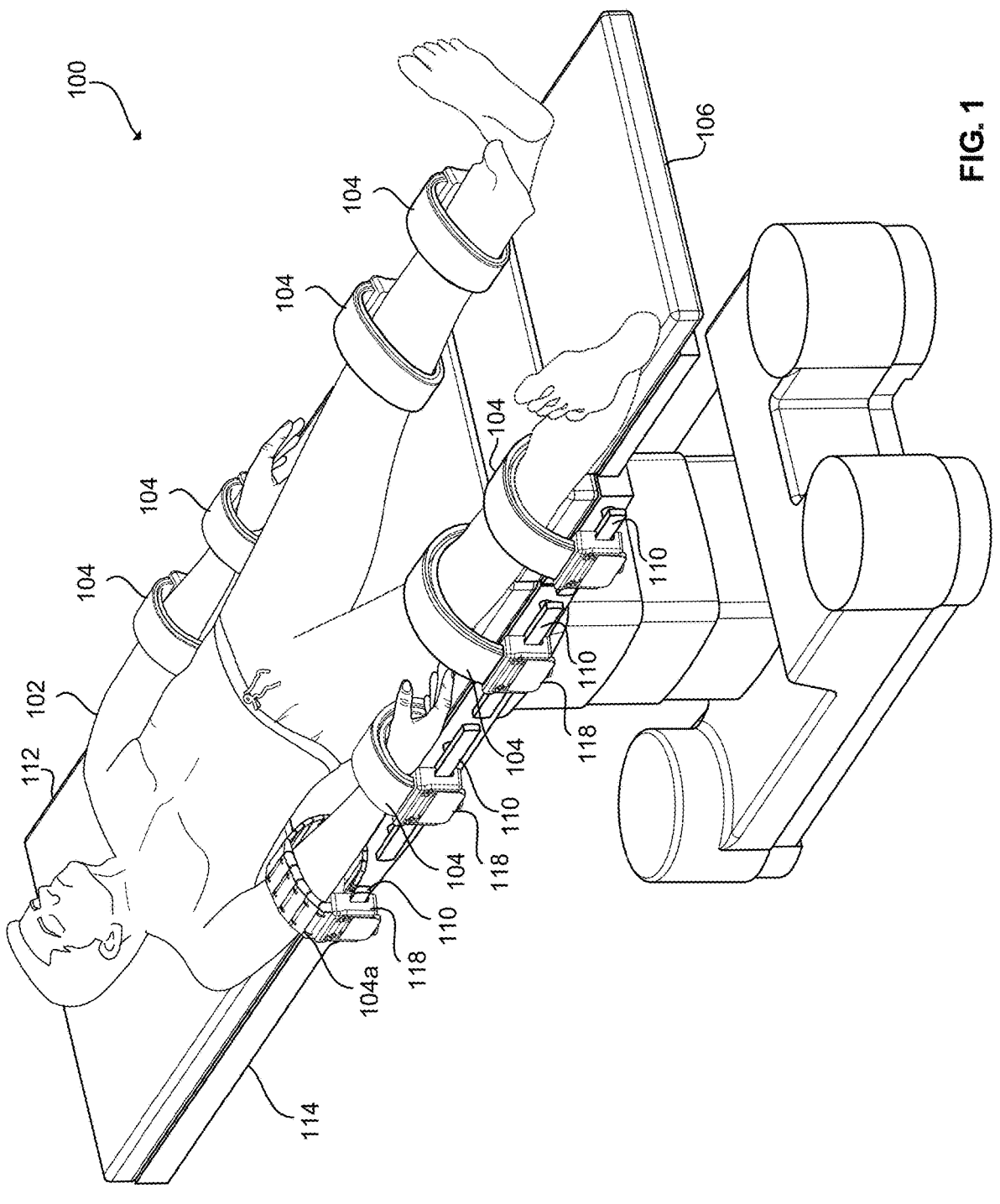
FIG. 1 shows a perspective view of an example system for positioning a patient, consistent with some embodiments of this disclosure.

Referring to FIG. 1, some embodiments of a system 100 for releasably maintaining a subject, such as a patient 102 that is sedated or otherwise prepared for medical assistance, in a selected position can include adjustable restraint devices 104 and a surgical table 106. In the depicted embodiment, the adjustable restraint devices 104 are adjustable limb restraints that are removably mated with portions of the surgical table 106 and that are manually adjustable to any of a variety of curved or other user-selected shapes for improved and comfortable engagement with limbs of the patient 102. The adjustable restraint devices 104 of the system 100 can releasably lock into the user-selected shape to safely hold the patient 102 in the selected position on the surgical table 106, which may reduce the likelihood of the patient 102 inadvertently moving out of the selected during a medical procedure. As detailed below (refer, for example, to FIGS. 5A-D and 6A-B), the adjustable restraint devices 104 can employ a series of links 140 having improved end connectors 145 and 146 that, in response to user adjustment of an actuator, can simultaneously and releasably lock adjacent links 140 in the user-selected shape.

Still referring to FIG. 1, the surgical table 106 can include one or more rails 110 that extend along each side of the surgical table 106. The one or more rails 110 can extend from each side of the surgical table 106. In some aspects, each side of the table 106 can include a plurality of rails 110 that are spaced apart along the length of the surgical table 106, while in other aspects, each side of the surgical table 106 can include a continuous rail 110 that extends along the length of the surgical table 106. For example, a left side 112 of the surgical table 106 can include four rails 110 spaced apart along the length of the surgical table 106, and a right side 114 of the surgical table 106 can include four rails 110 spaced apart along the length of the surgical table 106.

In the depicted embodiment, the system 100 includes a plurality of the adjustable restraint devices 104 that are slidably mated to the surgical table 106. Each adjustable restraint device 104 is adjustable and can be formed as a flexible cuff system to extend around a patient's limb (e.g., an arm, a leg, or a torso of a patient). Each adjustable restraint device 104 can be independently operable by a user so that each restraint device 104 can be separately controlled by a user as desired. As illustrated, the system 100 includes adjustable restraint devices in the size and form of adjustable limb restraints 104 positioned and formed around the arms and the legs of the patient 102. In the depicted embodiment, the system 100 includes two adjustable limb restraints 104 for each arm of the patient 102 and two adjustable limb restraints 104 for each leg of the patient 102. In other embodiments, the system 100 can include an adjustable limb restraint 104 for each limb of the patient 102. In other examples, the system 100 can include adjustable limb restraints 104 for the arms and not the legs or adjustable limb restraints 104 for the legs and not the arms.

Still referring to the depicted embodiment in FIG. 1, a first portion of the adjustable limb restraints 104 is positioned on the right side 114 of the surgical table 106, and a second portion of the adjustable limb restraints 104 is positioned on the left side 112 of the surgical table 106. In this embodiment, the system 100 includes four adjustable limb restraints 104 on the right side 114 and four adjustable limb restraints 104 on the left side 112. While four adjustable limb restraints 104 on each side of the surgical table 106 is shown, the system 100 is not limited to this arrangement. The system 100 can include one adjustable limb restraint 104, two or more adjustable limb restraints 104, or a plurality of adjustable limb restraints 104. The adjustable limb restraints 104 depicted in FIG. 1 preferably include a protective outer sleeve (described in more detail below) to provide a padded interface with the patient and to protect the interior mechanism of each adjustable limb restraint 104, but one adjustable limb restraint 104*a* is depicted in FIG. 1 with the protective sleeve removed from view for illustrative purposes. In some implementations, the protective sleeve is slidably removable from the adjustable limb restraint 104 so that the sleeve can be readily discarded in a sanitary manner after its use, and the remaining components of the adjustable limb restraint 104 can be receive a new protective sleeve for reuse in subsequent medical procedures.

In some embodiments, each of the adjustable limb restraints 104 can removably connect to one of the rails 110 of the surgical table 106. For example, each adjustable limb restraint 104 includes a handle body 118 that defines a recess that is configured to slidably mate the adjustable limb restraint 104 with at least one of the rails 110. In use, the adjustable limb restraints 104 are movable along the rails 110 to a user-selected position relative to the surgical table 106 (e.g., to customize the longitudinal position for patients of different sizes or in different positions), where the adjustable limb restraints 104 can be releasably locked into its selected position along the rail 110 during the medical procedure.

Figures 2A, 2B:
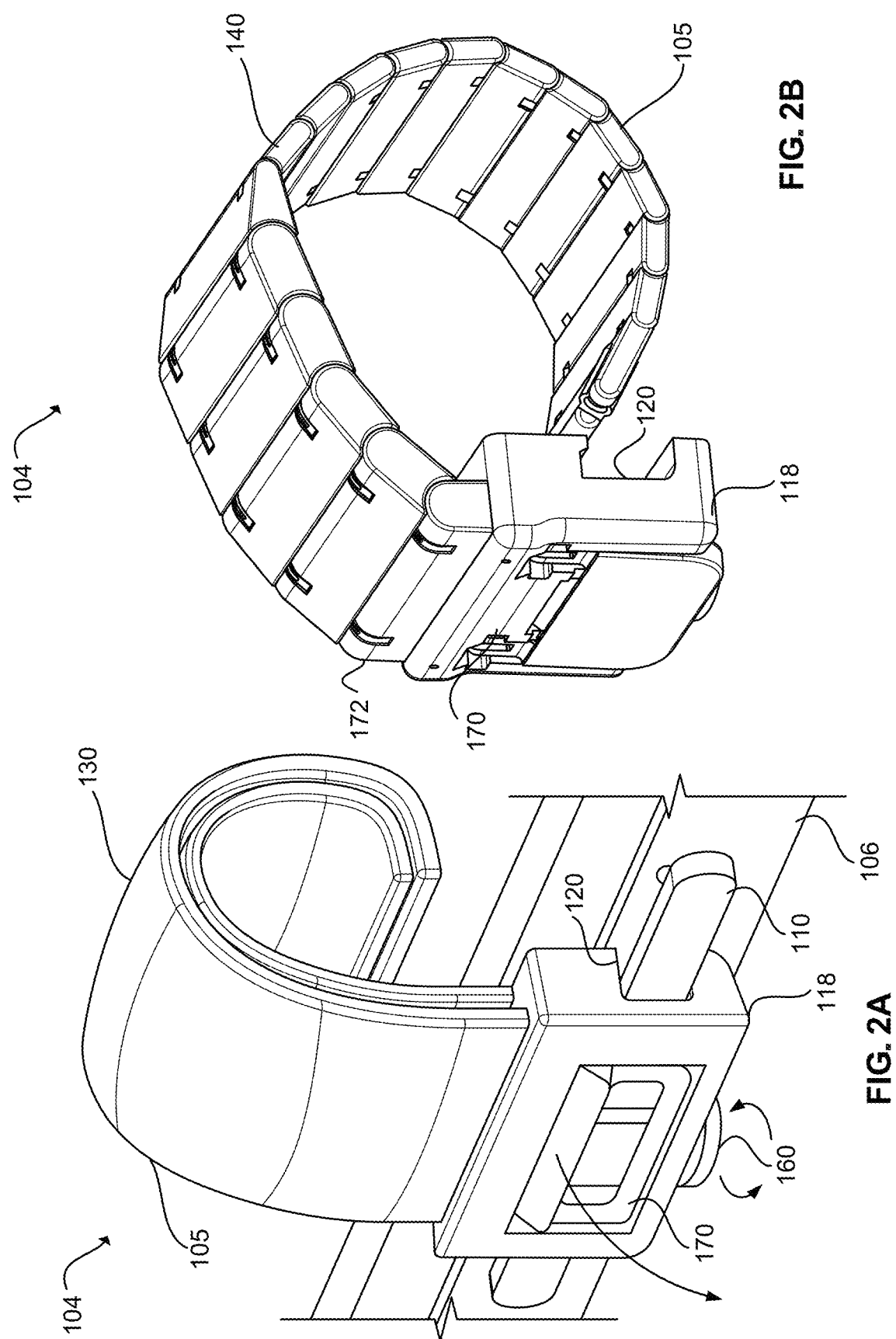
FIG. 2A shows a perspective view of an example adjustable limb restraint connected to a surgical table of the system of FIG. 1.
FIG. 2B a perspective view of the adjustable limb restraint of FIG. 2A with a protective sleeve removed from view.

Referring now to FIGS. 2A-B, some embodiments of the adjustable restraint device 104 can include the protective sleeve 130 and an interior mechanism 140 to releasably lock the restraint device 104 in a curved or otherwise user-selected, user-selected shape for comfortably engaging with a patient. FIG. 2A shows a perspective view of one of the adjustable limb restraints 104, which in this embodiment includes a flexible cuff body 105 extending distally from the handle body 118 toward a free end. The handle body 118 is connected to one of the rails 110 of the surgical table 106 of the system 100, as previously described in connection with FIG. 1. In this embodiment, the flexible cuff body 105 includes the protective sleeve 130 slidably positioned over an interior mechanism 140 (e.g., linkage assembly in this embodiment, as shown in FIG. 2B with the protective sleeve 130 removed from view for illustrative purposes) so as to provide a cushioned interface with the patient and to provide a sterile protective cover over the mechanical components of the mechanism 140. The protective sleeve 130 can include padding that can prevent pinching between the series of links 140, and the protective sleeve 130 can include a fluid impermeable outer material to facilitate rapid cleaning or removal of bodily fluid from the adjustable limb restraint 104.

In this embodiment, the flexible cuff body 105 (including the protective sleeve 130 and the mechanism 140) has an adjustable shape and can be releasably locked into a selected shape or unlocked for manual manipulation of the linkage assembly 140 (and the sleeve 130 therewith) to a different shape. In the depicted embodiment, the flexible cuff body 105 is in a curved configuration that is configured to extend around a limb of a patient (e.g., an arm, a leg, or a torso of the patient 102). The flexible cuff body 105 can be adjusted into customizable orientations to retain a limb of the patient 102, and the customizable orientations can include several different configurations, as shown and described below. As detailed below, the overall shape of the flexible cuff body 105 can be releasably locked in the user-selected orientation to maintain its shape for maintaining the patient's position during a surgical procedure The handle body 118 of the adjustable limb restraint 104 is configured to releasably lock the adjustable limb restraint 104 at a selected longitudinal position along the corresponding rail 110. The handle body 118 defines a mating interface surface 120 that is dimensioned to receive the rail 110 and slidably engage with the rail 110. In some aspects, the mating interface surface 120 is formed as a recess (e.g., oriented parallel to the rail 110) in the handle body 118 on a table side of the handle body such that the rail 110 extends through the mating interface surface 120 and remains in abutment with the handle body 118. In some aspects, the position of the adjustable limb restraint 104 along the rail 110 can be secured by an actuator of the handle body 118. For example, the handle body 118 can include a rotatable knob 160 (FIG. 2A), and the knob 160 can facilitate releasably locking the adjustable limb restraint 104 in a selected position along the rail 110. In this example, the adjustable limb restraint 104 can be slidably moved along the rail 110 via the interface between the rail 110 and the mating interface surface 120 to reach a selected longitudinal position along the rail 110. After reaching this position selected by the user, the knob 160 can be rotated to urge a shaft of the knob 160 (not shown) into an interference fit with the rail 110, thereby releasably locking the adjustable limb restraint 104 in the selected longitudinal position along the rail 110. To readjust the adjustable limb restraint 104 relative to the rail 110, the knob 160 can be rotated in an opposite direction (to loosen the knob 160), thereby allowing the movement (e.g., sliding movement) of the adjustable limb restraint 104 along the rail 110.

Still referring to FIGS. 2A-B, some embodiments of the adjustable restraint device 104 also include another actuator, which can be shifted by the user to releasably lock the mechanism 140 in a user-selected configuration. For example, in this embodiment, the adjustable limb restraint 104 includes an actuator in the form of handle 170 on the handle body 118, which can be pivoted to actuate a mechanical lock upon the series of links in the linkage assembly 140. As shown in FIG. 2B, the linkage assembly 140 extends from the handle body 118 in a direction away from the rail 110/mating interface surface 120, and the series of links in the linkage assembly 140 are pivotably connected to one another so that the overall length of the linkage assembly 140 can be manually adjusted from a first position (e.g., a vertically straight configuration such as that of FIG. 3 or other shape that is oriented away from patient location on the surgical table 106) to a second position (e.g., curved or otherwise customized to wrap around a targeted portion of the patient). As such, the relatively rotational adjustment of the adjacent links in the series of links 140 extending away from the handle body 118 facilitates the ability for a user to change the angle of the adjustable limb restraint 104 (e.g., toward a non-parallel angle with respect to the side surface of the rail 110 and the surgical table 106) and to change the shape of the adjustable limb restraint 104 (e.g., toward a curved configuration in the depicted embodiment). Additionally or alternatively, the adjacent links in the series of links 140 can be linked together via one or more movable joints that provide motion beyond a hinged connection, including for example, a pivot point connection or a ball-and-socket component to provide multiple degrees of freedom between the adjacent links in the series of links 140. For example, the adjacent links in the series of links 140 can be linked together via one or more cables and engagement teeth that are actuated between locked and unlocked states to facilitate the ability for a user to change the angle of the adjustable limb restraint 104 into a desired position and locking the adjustable limb restraint 104 in the desired position.

In the depicted embodiment, the handle actuator 170 of the handle body 118 can be used to shift the flexible cuff body 105 between the locked and unlocked positions. The handle 170 can be positioned on an exterior facing side of the handle body 118 so that the handle 170 is accessible to a user while the adjustable limb restraint 104 is connected to the surgical table 106. The handle 170 can control a tension element or other lock instrument that acts upon the series of links 140 extending from the handle body 118. In some aspects, the series of links 140 are connected to the handle body 118 via a base 172, which extends upwardly away from the mating interface 120 of the handle body 118.

The handle 170 is movable between an unlocked position (refer to FIG. 2A) and a locked position (refer to FIG. 2B). For example, the handle 170 can be shifted from the unlocked position (FIG. 2A) to the locked position (FIG. 2B) by grasping the handle 170 and pivoting it downwardly away from the base 172 and the initial link of the linkage system 140. When the handle 170 is in the unlocked position, the flexible cuff body 105 is manually adjustable to a user's selected position, such as the curved configuration depicted in FIG. 2B. For example, with the handle 170 in the unlocked position, a user can adjust the overall shape of the flexible cuff body 105 (and the configuration of the series of links 140) to achieve a user-selected configuration that fits with any patient among a variety of different patient sizes, different limb types, and different limb arrangements relative to the surgical table 106 (or, alternatively, to release away from the patient after use). In some aspects, the series of links 140 are each configured to pivot with respect to each other to provide for a plurality of degrees of freedom that user can form the series of links 140 into various shapes and sizes. When the handle 170 is shifted to the locked position, the flexible cuff body 105 is releasably locked in the user-selected configuration, such as the curved configuration depicted in FIG. 2B. For example, after the flexible cuff body 105 is maneuvered or adjusted by a user into a user-selected configuration (while handle 170 is in the unlocked position), the flexible cuff body 105 can be locked and thereafter fixed in that user-selected configuration (by shifting the handle 170 to the locked position).

Accordingly, some embodiments of the adjustable limb restraints 104 can be releasably locked in a wide number of customizable positions as selected by a user (e.g., a surgeon, a nurse, a physical therapist, a doctor, a surgical technician, veterinarian, or other user) to achieve a safe and comfortable apparatus for maintaining the patient's position on the surgical table 106. Examples of patient positions that can be maintained by the adjustable limb restraints 104 include, but are not limited to supine, prone, lateral decubitus, lateral recumbent.

Figure 3:
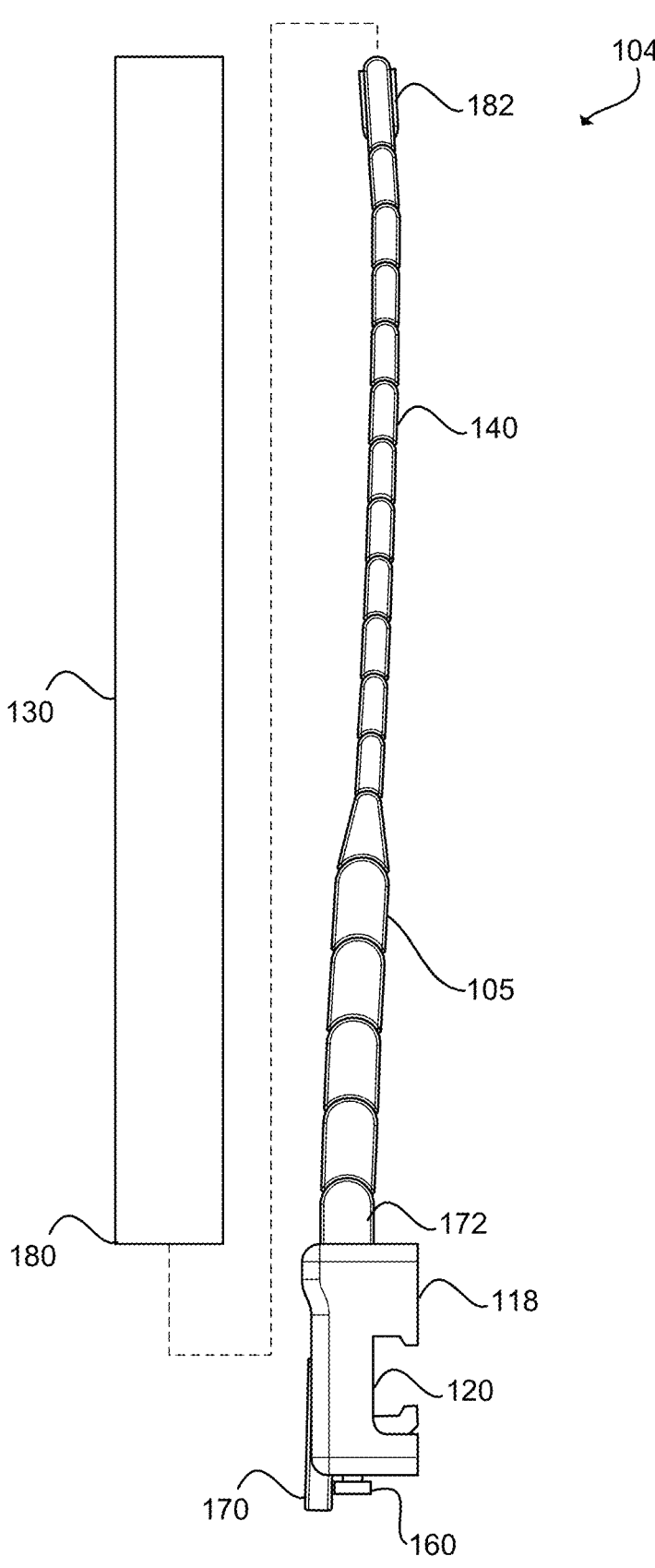
FIG. 3 shows an exploded side view of the adjustable limb restraint of FIGS. 2A-B.

Referring now to FIG. 3, some embodiments of the adjustable limb restraint 104 include a slidably removable form of the protective sleeve 130, which includes an interior pocket configured to receive the free end of the linkage assembly 140. The protective sleeve 130 can be a padded sleeve that extends around the series of links 140. For example, a proximal end 180 of the protective sleeve 130 can include an opening into the interior pocket space so that the protective sleeve 130 can be pulled over a distal-most end link 182 of the series of links 140. The protective sleeve 130 can be advanced over the series of links 140 until the proximal end 180 covers the base 172. As previously described, the protective sleeve 130 can include padding that can provide cushioning and comfort for the patient and furthermore prevent pinching between the series of links 140, and the protective sleeve 130 can include a fluid impermeable outer material to facilitate rapid cleaning of the adjustable limb restraint 104. In some circumstances, the protective sleeve 130 can remain on the adjustable limb restraint 104 during a cleaning or sterilization process, or in other implementations, the protective sleeve 130 can be removed from the adjustable limb restraint 104 for cleaning or sterilization. Additionally or alternatively, the protective sleeve is slidably removable from the linkage assembly 140 so that the sleeve 130 can be readily discarded in a sanitary manner after use with a first patient, and the remaining components of the adjustable limb restraint 104 can be receive a new protective sleeve for reuse in a subsequent medical procedure (e.g., with a different patient). As shown in FIG. 3, the adjustable limb restraint 104 can be arranged in the vertical configuration (extending upwardly away from the handle body 118) so that linkage assembly 140 extends away from the surgical table 106. This vertical configuration can facilitate insertion or removal of the protective sleeve 130. Additionally, in some circumstances, this vertical configuration can use temporarily employed while the patient is being loaded onto the surgical table, while the patient is being removed from the table, during a period of time of medical imaging in the area of the patient's limb near adjustable limb restraint 104.

Figure 4:
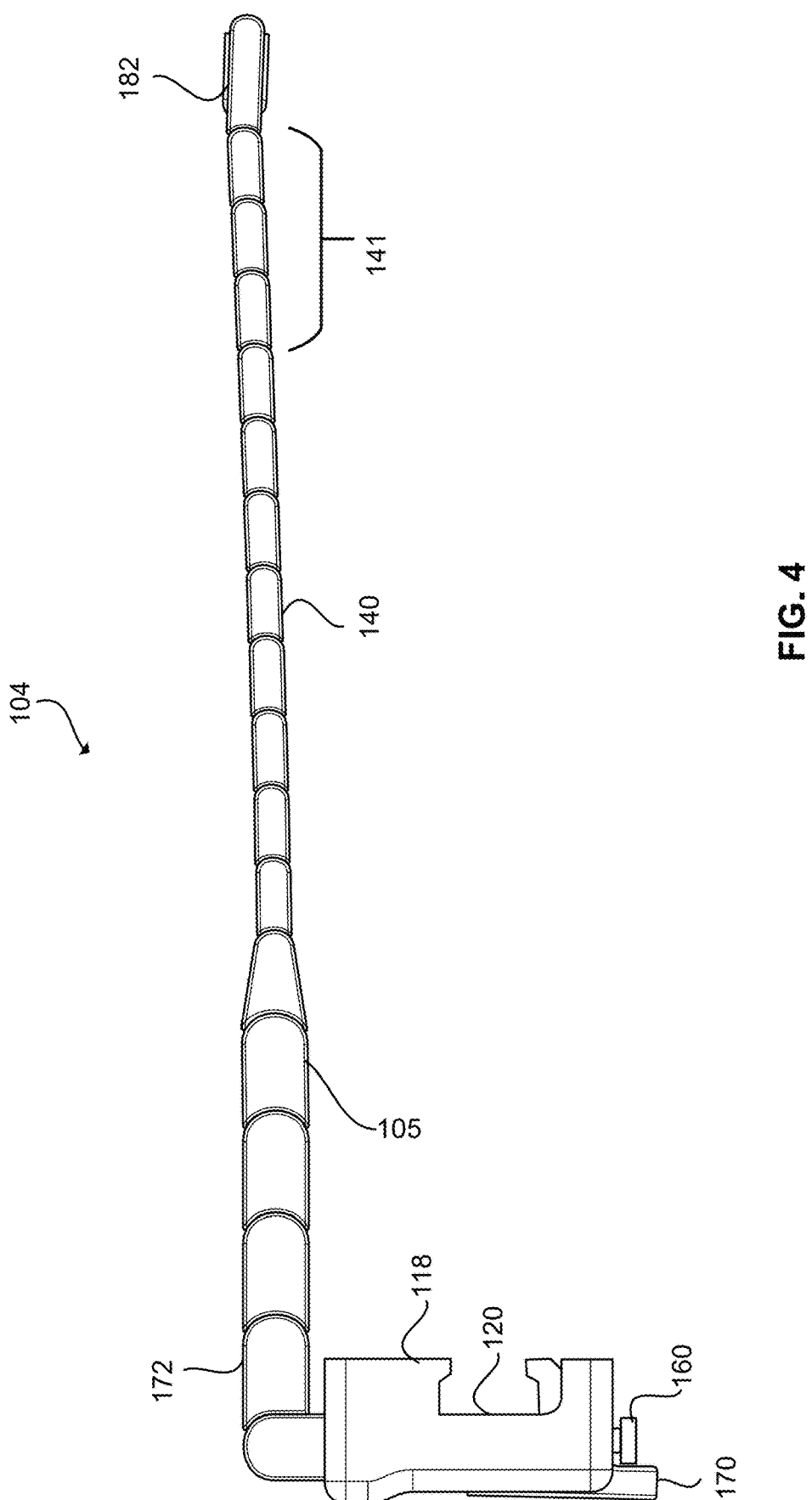
FIG. 4 shows the adjustable limb restraint of FIG. 3 in another position.

Referring now to FIG. 4, the adjustable limb restraint 104 (depicted with the protective sleeve removed from view for illustrative purposes) can be arranged in a horizontal configuration, in which the series of links in the linkage assembly 140 extend in a direction generally perpendicular to the configuration depicted in FIG. 3. In some aspects, the horizontal position of the adjustable limb restraint 104 can allow the adjustable limb restraint 104 to lie flat on the surgical table 106, for example, while that portion of the surgical table is unoccupied.

Referring now to FIGS. 5A-D and 6A-B, some embodiments of the adjustable limb restraint 104 can include a linkage assembly 240 equipped with improved end connectors 145 and 146 that releasably mate (in response to movement of the handle actuator 170) to releasably lock the adjacent links together with an increased locking strength and torque resistance. In some embodiments, the linkage assembly 240 can replace the linkage assembly 140 of the adjustable limb restraint 104. While a portion 241 of the linkage assembly 240 is shown, the linkage assembly 240 can include any number of links, including the same or similar number of links as the linkage assembly 140. For example, the portion 241 of the linkage assembly 240 can replace the portion 141 of the linkage assembly 140 in FIG. 3. In the depicted embodiment, a portion 241 of the linkage assembly 240 is shown with some of the links of the linkage assembly 240 removed from view. For example, the portion 241 of the linkage assembly 240 can include any portion of links throughout the linkage assembly 240 (e.g., a portion 141 of links near the distal end of the linkage assembly 140 as illustrated in FIG. 3). It should be understood from the description herein that the features of the portion 241 of the linkage assembly 240 can be applicable to the entire linkage assembly 240, or to portions of the linkage assembly 240.

In this embodiment, each of the links 142a-c of the linkage assembly 240 can include a pair of first end connectors 145 positioned along opposing axial ends of the link body 143 and a pair of second end connectors 146 extending from a lateral bracket 149 of the link body 143. As described in more detail below, in this depicted example of the first end connectors 145 can be in the form a beveled spline receiver having set of splines or teeth along an interior conical face, and each pair of beveled spline receivers 145 are axially aligned along a first axis 147 of the link body 143. Also, in this example, the second end connectors 146 can be in the form of a beveled spline having a corresponding set of teeth along an exterior conical face, and each pair of beveled splines 146 are axially aligned along a second axis 153 of the lateral bracket 149. Each of the links 142a-c of the linkage assembly 240 are pivotable with respect to each adjacent link about a pivot axis corresponding to the axis where second end connectors 146 mate with the first end connectors 145 (e.g., either the first axis 147 or the second axis 153), which thereby facilitates the user selection of various customized orientations of the linkage assembly 240 (until the linkage assembly is locked). As shown in FIGS. 5A-D, the link 142*a* is connected to a link 142*b*, which is connected to a link 142*c*, and this series can continue for a greater number of links. In the illustrated embodiment, the link 142*a* is shown with one adjacent link removed (e.g., on the side of the link 142*a* opposite the link 142*b*). The links 142*a*, 142*b*, and 142*c* can share features with each other that facilitate the connection of the links 142*a*-142*c* (and other similar links) to form the portion 241 of the linkage assembly 240. While the link 142*c* is shown connected to an end link 148, the link 142*c* can be replaced with any number of additional links to form the linkage assembly 240. Additionally or alternatively, any number of links can be connected to the link 142*a* to form the linkage assembly 240. In some embodiments, the end link 148 of the portion 241 of the linkage assembly 240 can replace the distal most end link 182 of the linkage assembly 140. The end link 148 can facilitate a connection to another end link or linkage assembly. For example, the end link 148 can be configured for connection to another end link (e.g., another end link 148) to connect the linkage assembly 240 to another linkage assembly (see e.g., FIG. 8A).

Referring to FIGS. 5A-D and 6A-B, the improved end connectors 145 and 146 can be implemented in a manner so that all of the end connectors 145 and 146 are responsive to the user-actuated movement of the handle actuator 170 to simultaneously and releasably lock the adjacent links together with an increased locking strength and torque resistance. each of the links 142*a*-142*c* includes first end connectors 145 on each side of the links 142*a*-142*c*, the first end connectors 145 can be in the form a beveled spline receiver having set of splines or teeth along an interior conical face. The links 142*a* and 142*b* include second end connectors 146 that extend from each side of a bracket 149 connected to the links 142*a* and 142*b*, the second end connectors 146 can be in the form of a beveled spline having a corresponding set of teeth along an exterior conical face. Adjacent links (e.g., links 142*a*, 142*b*) are connected together by inserting the second end connectors 146 of one link (e.g., link 142*a*) into the first end connectors 145 of the adjacent link (e.g., link 142*b*).

The first end connectors 145 have a tapered profile that is configured to receive a tapered profile of the second end connectors 146. The first end connectors 145 are recessed into each lateral side of the links 142*a*-142*c*, and the recessed area of the first end connectors 145 has a tapered profile that is widest at an outer edge of the first end connectors 145 and narrowest at an inner most portion of the recessed area of the first end connectors 145.

The second end connectors 146 extend from opposing inner facing surfaces 150 of the bracket 149. The bracket 149 extends along a bottom surface of each of the links and includes flexible regions 151 on each side of the bracket 149 that extend from the first end connectors 145 and connect to the inner facing surfaces 150 of the bracket 149. The bracket 149 extends from the link such that the second end connectors 146 of each link are positioned generally below the first end connectors 145 (e.g., in the orientation illustrated in FIGS. 5A-5D). For example, the flexible regions 151 of the bracket 149 extend inwardly from the first end connectors 145 and include a curved portion 152 at an inner most area of the flexible regions 151. The curved portion 152 can turn the flexible region 151 from an inwardly extending direction to and outwardly extending direction where the flexible region 151 extends from the curved portion 152 outwardly to the inwardly facing surface 150. For example, the curved portion 152 can include a 180 degree turn that turns the flexible region 151 from an inwardly extending direction to and outwardly extending direction.

Still referring to FIGS. 5A-D and 6A-B, the flexible regions 151 of the bracket 149 facilitate deflection of the second end connectors 146 and the inner facing surfaces 150. For example, the flexible regions 151 (e.g., including the curved portions 152) can be a cantilevered spring that deflects responsive to forces applied in the x axis or the y axis (see e.g., FIGS. 7A-E). The cantilevered spring geometry of the flexible regions 151 of the bracket 149 facilitates engagement and disengagement of the second end connectors 146 from each other that releasably locks the linkage assembly 240 into a user-selected shape or unlocks for manual manipulation of the linkage assembly 240 to a different shape.

The second end connectors 146 have a tapered profile that is widest at the inner facing surfaces 151 of the bracket 149 and narrowest at the inner most end of the second end connectors 146. The narrowest portion of the second end connectors 146 is configured to be inserted into the narrowest portion of the first end connectors 145 (e.g., at the inner most portion of the first end connectors 145). The second end connectors 146 and the first end connectors 145 are configured to be compatible with each other so that the second end connectors 146 and the first end connectors 145 facilitate releasably locking adjacent links in position and adjusting the position of the links with respect to each other into various user-selected orientations.

The inner facing surfaces 150 of the bracket 149 position the second end connectors 146 generally below the first end connectors 145 to facilitate the connection of the links to each other to form the linkage assembly 240. For example, an adjacent link is configured to be received between the inward facing surfaces 150 of the bracket 149, with the second end connectors 146 being received by the first end connectors 145 of the adjacent link. The first end connectors 145 can form a beveled spline receiver having set of splines or teeth along an interior conical face of the first end connectors 145, and the second end connectors 146 can form a beveled spline having a corresponding set of teeth along an exterior conical face. Each pair of beveled spline receivers at the first end connectors 145 are axially aligned along a first axis 147 of the link body 143 and can receive a corresponding pair of second connectors 146 from an adjacent bracket 149 so that the second axis 153 of the second connectors 146 of the adjacent link (e.g., link 142*c*) aligns with the first axis 147 of the link (e.g., link 142*b*).

Still referring to FIGS. 5A-D and 6A-B, each link (e.g., links 142*a*, 142*b*, 142*c*) includes one or more openings that are configured to receive one or more cables that extend through the one or more openings. In some embodiments, each link (e.g., links 142*a*, 142*b*, 142*c*) includes a first opening 155 that is positioned along the link body 143 between the first end connectors 145 at each end of the link. In the depicted embodiment, the first opening 155 is at or nearly centered along the link body 143. The linkage assembly 240 includes a plurality of first openings 155 in each link body 143 of the linkage assembly 240. The plurality of first openings 155 are aligned with each other so that a single longitudinal cable can extend through the plurality of first openings 155 (see e.g., FIGS. 7A-D).

In some embodiments, each link (e.g., links 142*a*, 142*b*, and 142*c*) and each bracket 149 includes lateral openings 157 on opposing sides of the bracket 149. The lateral openings 157 extend through the bracket 149 to the inner facing surfaces 150 and through the second end connectors 146. The lateral openings 157 on each side of the bracket 149 are aligned with each other (e.g., along the second axis 153) so that a transverse cable can extend between the lateral openings 157 at each link. In some embodiments, each link can define an opening or passageway so that the lateral openings 157 can be aligned with each other for a longitudinal cable to connect the lateral openings 157 along the second axis 153. For example, each link can be generally hollow and have an open space that facilitates a connection between each lateral opening 157.

Referring to FIGS. 7A-D, some embodiments of the adjustable limb restraint 104 can include one or more tensioners or lock instruments that engage with the series of links in the linkage assembly 240 to releasably lock the linkage assembly 240 in the selected position (in response to actuation of the handle 170). For example, the adjustable limb restraint 104 can include a longitudinal cable 190 that extends from the handle body 118 through the series of links 140 of the flexible cuff body 105 and a plurality of transverse cables 192 that extend across each link of the series of links 140 and connect to the longitudinal cable 190. In some aspects, the adjustable limb restraint 104 can include a longitudinal cable 190 that extends through the plurality of first openings 155 in each link body 143 in the series of links 140. In the depicted embodiment, the adjustable limb restraint 104 can include a single longitudinal cable 190. In another example, the adjustable limb restraint 104 can include two or more longitudinal cables. For example. The adjustable limb restraint 104 can include two longitudinal cables 190 (e.g., a right side cable and a left side cable), and the two longitudinal cables 190 may extend parallel to each other as they extend through the series of links 140.

In some aspects, the adjustable limb restraint 104 includes the plurality of transverse cables 192. Each of the transverse cables 192 extends through a link from one side to the opposing side (e.g., along the first axis 147 of the link body 143). For example, each transverse cable 192 extends through each lateral opening 157 at each bracket. The transverse cables 192 can be connected to the bracket 149 such that the transverse cables 192 extend across a width of the linkage assembly 240. For example, the transverse cables 192 can include fasteners 193 on the outside of the bracket 149 that secure the transverse cables 192 to the bracket 149. In some embodiments, the fasteners 193 can be secured within the lateral openings 157, or can be secured an outer face of the bracket 149 (e.g., by having a larger size than the lateral openings 157).

In some embodiments, the transverse cables 192 can facilitate a connection between adjacent links. For example, the transverse cables 192 can extend through the lateral openings 157 of the bracket 149 of a first link (e.g., link 142a) and into an adjacent link (e.g., link 142b) that is positioned between inner facing surfaces 150 of the bracket 149 of the first link. In this example, the transverse cable 192 extends along the second axis 153 of the bracket 149 of the link 142 and along the first axis 147 of the link 142b. In a connected configuration, the first axis 147 of the link 142b is aligned with the second axis 153 of the link 142a. The transverse cables 192 can extend through the bracket 149 and the second end connectors 146 of the first link and through the first end connectors 145 of the adjacent link.

In some embodiments, the longitudinal cable 190 can connect to each of the transverse cables 192. For example, the longitudinal cable 190 can include plurality of fasteners 194 positioned along the longitudinal cable 190 to connect to each transverse cable 192. The fasteners 194 can include ties, knots, clips, screws, pins, or other fasteners that connect the longitudinal cable 190 to each transverse cable 192. In some embodiments, the fasteners 194 can facilitate a connection between the longitudinal cable 190 and each transverse cable 192 so that, responsive to a locking actuation of the longitudinal cable 190 (e.g., via actuation of the handle 170), each of the transverse cables 192 are actuated by the longitudinal cable 190.

Referring to FIGS. 7A-D and to FIGS. 2A-B, the handle 170 can be connected to the longitudinal cable 190 such that actuation of the handle 170 causes an adjustment of the longitudinal cable 190. As such, the actuation of the handle 170 from the unlocked position to the locked position can urge the longitudinal cable 190 to impart a force to the series of links in the linkage assembly 240 that locks the links in the selected position. For example, when the handle 170 is actuated to the locked position, the handle 170 can apply a tensile force 201 on the longitudinal cable 190. The tensile force 201 on the longitudinal cable 190 generates tensile forces 202 at each transverse cable 192 via the connection of each transverse cable 192 to the longitudinal cable 190. The tensile forces at each transverse cable 192 can cause each transverse cable 192 to deflect from an unlocked position (see e.g., FIG. 7A) into a locked position (see e.g., FIGS. 7B-C).

The tensile forces at each transverse cable 192 and resulting deflection of each transverse cable 192 generates compressive forces 203 at each fastener 193. The compressive forces 203 compress the second end connectors 146 against the first end connectors 145 that impart tensile forces 204 against the second end connectors 146. The compressive forces 203 and the tensile forces 204 compress the second end connectors 146 and the first end connectors 145 together to create a frictional engagement, thereby retaining each link in linkage assembly 240 in a fixed position relative to each adjacent link. In some embodiments, the flexible regions 151 of each bracket 149 facilitate a deflection of the flexible regions 151 in the z-axis (see e.g., FIG. 7E) responsive to the compressive forces 203. The deflection of the flexible regions 151 allows for movement of the second end connectors 146 towards the first end connectors 145. In the locked position (see e.g., FIGS. 7B-C), the second end connectors 146 and the first end connectors 145 are compressed together to prevent relative rotation between the second end connectors 146 and the first end connectors 145. For example, in the locked positon, the second end connectors 146 and the first end connectors 145 are prevented from pivoting past each other and the second end connectors 146 and the first end connectors 145 bind against each other to secure the linkage assembly 240 in position.

When the handle 170 is shifted to the unlocked position, the tension in the longitudinal cable 190 is released, thereby withdrawing the fixation caused by the frictional engagement between the links and allowing adjustment of the configuration of linkage assembly 240. In the unlocked position (see e.g., FIG. 7A), the second end connectors 146 and the first end connectors 145 may remain in contact with each other, and the compressive forces 203 are released to allow pivotal movement between the second end connectors 146 and the first end connectors 145. For example, in the unlocked positon, the second end connectors 146 and the first end connectors 145 are able to pivot past each other and the second end connectors 146 to facilitate forming the linkage assembly 240 into various user-selected shapes and sizes.

Figure 6A:
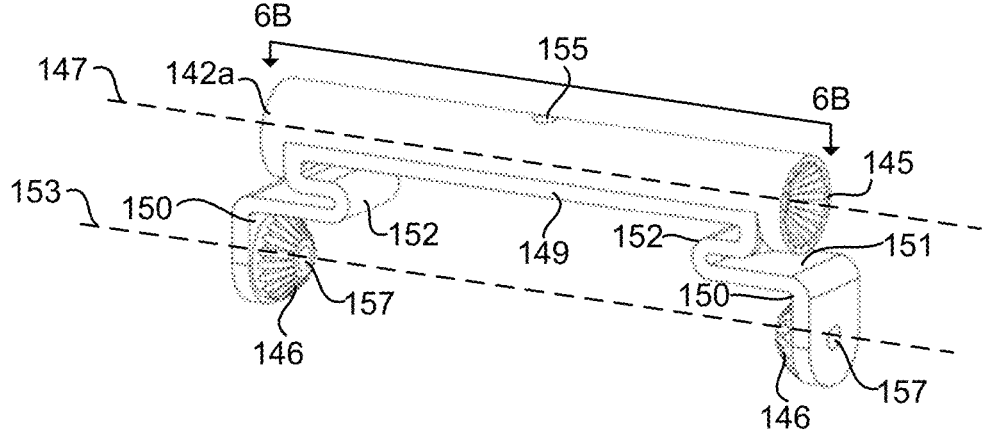
FIG. 6A shows a perspective view of an example link of the adjustable limb restraint of FIGS. 2A-B and 5A-D, with a section line 6B-6B.
Figure 6B:
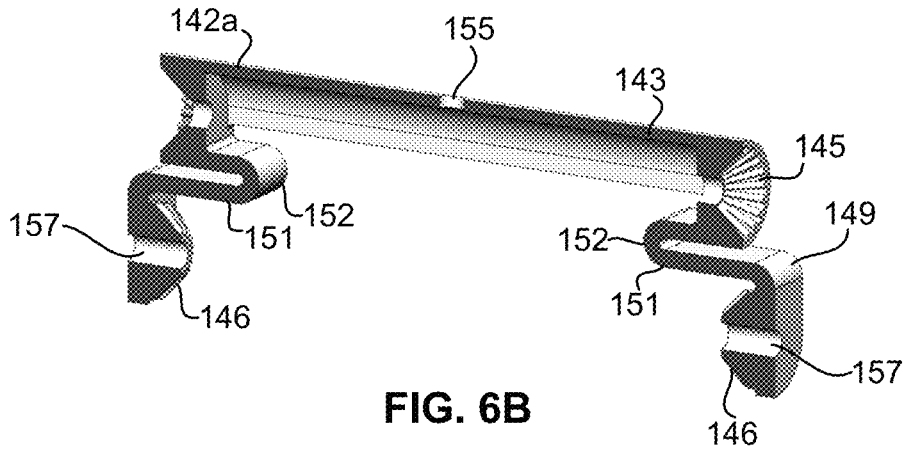
FIG. 6B shows a perspective cross-sectional view the example link along the section line 6B-6B from FIG. 6A.
Figures 7A, 7B, 7C:
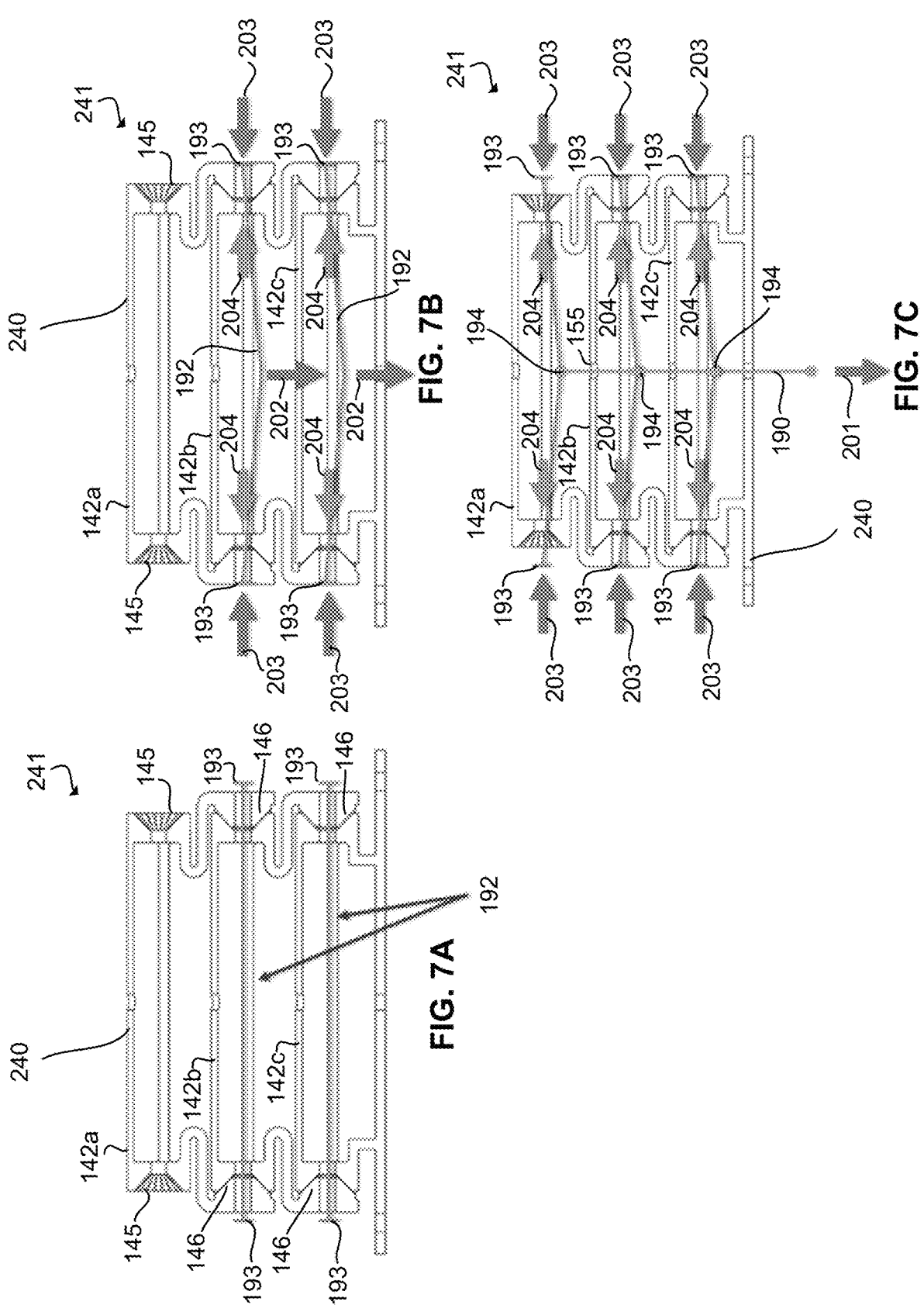
FIG. 7A shows the front view of FIG. 5A with example transverse cables shown in an example relaxed position.
FIG. 7B shows the front view of FIG. 5A with example transverse cables shown in an example locked position.
FIG. 7C shows the front view of FIG. 7B with an example longitudinal cable shown.
Figure 7D:
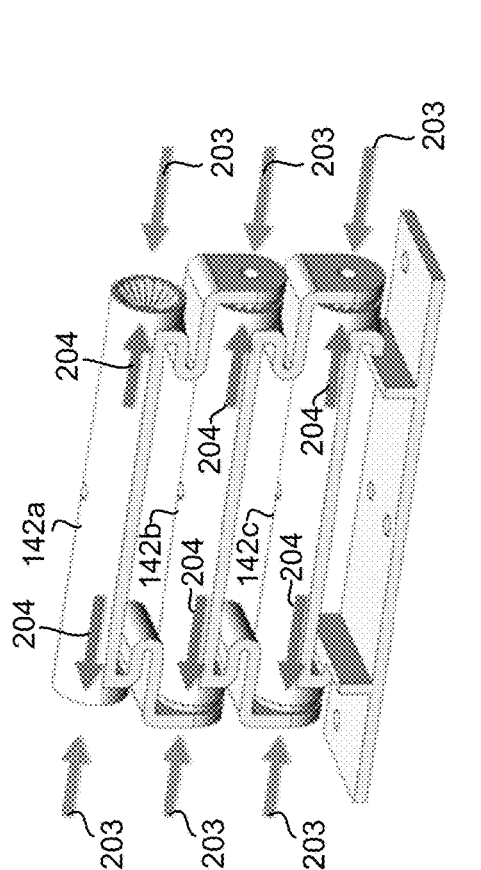
FIG. 7D shows the perspective view of FIG. 5A with example force vectors overlaid on the example adjustable limb restraint.
Figure 7E:
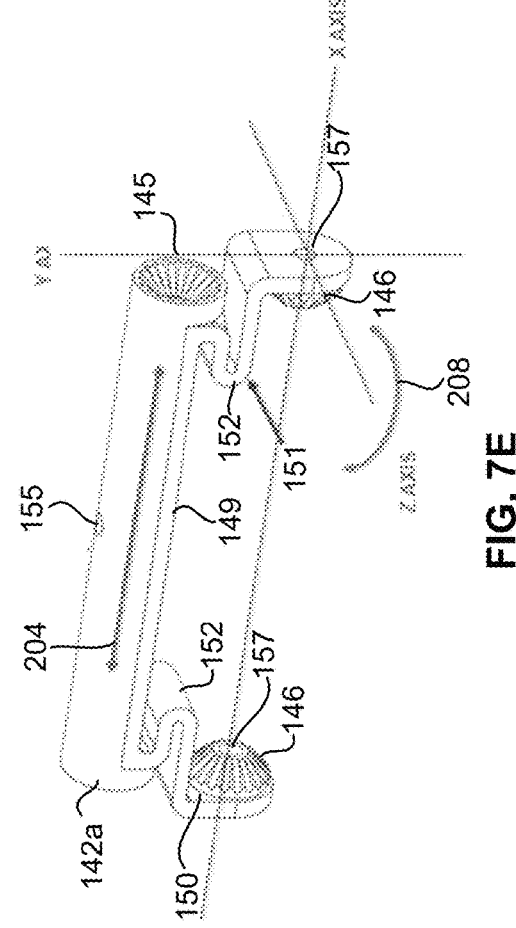
FIG. 7E shows the perspective view of FIG. 6A with example force vectors overlaid on the example link.

FIG. 7E shows the perspective view of FIG. 6A with example force vectors overlaid on one of the links (e.g., link 142a) of the linkage assembly 240. In some embodiments, the link body 143 is a rigid body that is subjected to the compressive forces (e.g., compressive forces 203). Responsive to the compressive forces 203 on each side of the link 142a, the link body 143 exerts tensile forces 204 to oppose the compressive forces 203. The tensile forces 204 and the compressive forces 203 can be aligned with the x-axis illustrated in FIG. 7E and with the first axis 147 illustrated in FIG. 6A.

The flexible regions 151 of the bracket 149 facilitate deflection of the second end connectors 146 and the inner facing surfaces 150. For example, the flexible regions 151 (e.g., including the curved portions 152) can be a cantilevered spring that deflects in direction 208 about the z-axis responsive to forces applied in the x axis, first axis 147, or the y axis (see e.g., FIGS. 6A and 7A-E). The cantilevered spring geometry of the flexible regions 151 of the bracket 149 facilitates engagement and disengagement of the second end connectors 146 from each other that releasably locks the linkage assembly 240 into a selected shape or unlocks for manual manipulation of the linkage assembly 240 to a different shape.

As previously described, the flexible cuff body 105 can be formed into various customizable shapes and sizes by manipulating the flexible cuff body 105 in the unlocked position. For example, the series of links 140 of the flexible cuff body 105 can define an opening sized to fit a patient's limb therein. Manipulating the flexible cuff body 105 into various shapes and sizes can adjust the overall shape and size of the opening. For example, the series of links 140 of the flexible cuff body 105 can be formed into an open ended hook. The open ended hook can begin at the base 172 and terminate at the end link 182. The open ended hook can extend vertically at the base 172 and can turn outwardly (i.e. away from the table side) to extend the opening for the patient's limb away from the table side. The series of links 140 can extend in a curved pattern to terminate in the end link 182, where the end link 182 is positioned closer to or above the table (e.g., surgical table 106) and the base 172 is positioned slightly lower than the end link 182.

Various configurations of the flexible cuff body 105 can be formed. For example, FIG. 1 shows the adjustable limb restraints 104 formed in closed-end loop configurations where the adjustable limb restraints 104 form a closed-end loop with the adjustable limb restraint 104 or with the surgical table 106. The closed loop can prevent a patient's limb from slipping out of the adjustable limb restraints 104. FIGS. 3 and 4 illustrate other configurations (e.g., vertical and horizontal configurations) of the adjustable limb restraints 104. Other example configurations include, but are not limited to, a conical shape where one end of the series of links 140 may have a smaller diameter than the other. In some examples, the adjustable limb restraint 104 can include several (e.g., 4-6, or more) smaller loosely connected individual linkage systems that could be manipulated to fit a patient's limb more closely.

FIG. 8A shows an end view of another example system 600 for positioning a patient. In the illustrated embodiment, the system 600 includes a first adjustable limb restraint 604a on a first side of a surgical table 606 and a second adjustable limb restraint 604b on a second (opposite) side of the surgical table 606. In the depicted embodiment, the protective sleeve (described above) for each restraint device 604a, 604b is removed from view for illustrative purposes. Each adjustable limb restraint 604a and 604b can share features with the adjustable limb restraints 104 described in detail above. For example, each adjustable limb restraint 604a, 604b can include a handle body 618a, 618b that connects to a corresponding rail 610 of the surgical table 606. As shown in FIG. 8A, the adjustable limb restraints 604a and 604b are sized and positioned to extend over the surgical table 606 so that the respective free ends meet one another. Optionally, the protective sleeve for each adjustable limb restraint 604a, 604b can provide distal end access to fasteners positioned at an end link 682a, 682b (refer also to FIGS. 6B-C) of each adjustable limb restraint 604a, 604b. Accordingly, the free ends of the opposing limb restraints 604a, 604b can be secured to one another, the adjustable limb restraints 604a, 604b can extend across the surgical table 606 and over a torso of the patient to releasably secure the patient in a selected position on the surgical table 606.

In some embodiments, the adjustable limb restraints 604a, 604b can extend across the surgical table 606 and over a torso of the patient to releasably secure the patient in a selected position on the surgical table 606 and provide protection to the patient. For example, the adjustable limb restraints 604a, 604b can extend across the surgical table 606 and over a torso of the patient and provide a rigid surface above the torso of the patient. The rigid surface provided by the adjustable limb restraints 604a, 604b can protect portions of the subject (e.g., the torso, limbs, etc.) from abrasions, burns, cuts, bruising, and other unnecessary contact with the patient in the area of the adjustable limb restraints 604a, 604b.

As shown in FIGS. 8B-C, the end links 682a, 682b of the opposing the adjustable limb restraints 604a, 604b can be configured to secure with one another via magnetic or mechanical connections. For example, in FIG. 6B, the end links 682a, 682b are configured to connect to each other via magnets 684a, 684b in each end link 682a, 682b. The magnets 684a, 684b provide a releasable connection between the end links 682a, 682b. Alternatively or additionally, as shown in FIG. 8C, the end links 682a, 682b are configured to connect to each other via fasteners 686a, 686b in each end link 682a, 682b. For example, the fasteners 686a can include a female receptacle and the fasteners 686b can include a male connector that is dimensioned to fit in the female receptacle of the fastener 686a. The fasteners 686a, 686b provide a releasable connection between the end links 682a, 682b.

In some embodiments, the adjustable limb restraints 604a, 604b (and the adjustable limb restraints 104) can incorporate temperature control elements that enable the adjustable limb restraints to aid in the management of the temperature and comfort of the patient. For example, the adjustable limb restraints 604a, 604b (and the adjustable limb restraints 104) can include one or more heating elements that can be heated to provide a warming effect to the patient at the adjustable limb restraints. In some embodiments, the temperature control elements can be pneumatic controls (e.g., environmentally conditioned air, fluid, and/or gas) that can be dispersed throughout the adjustable limb restraints. For example, the protective sleeve 130 can be connected to a blower assembly that is configured to supply environmentally conditioned air or gas to the protective sleeve to heat or cool the adjustable limb restraints. The protective sleeve can be pneumatically sealed so that fluid or gas does not escape the protective sleeve 130.

Figure 9A:
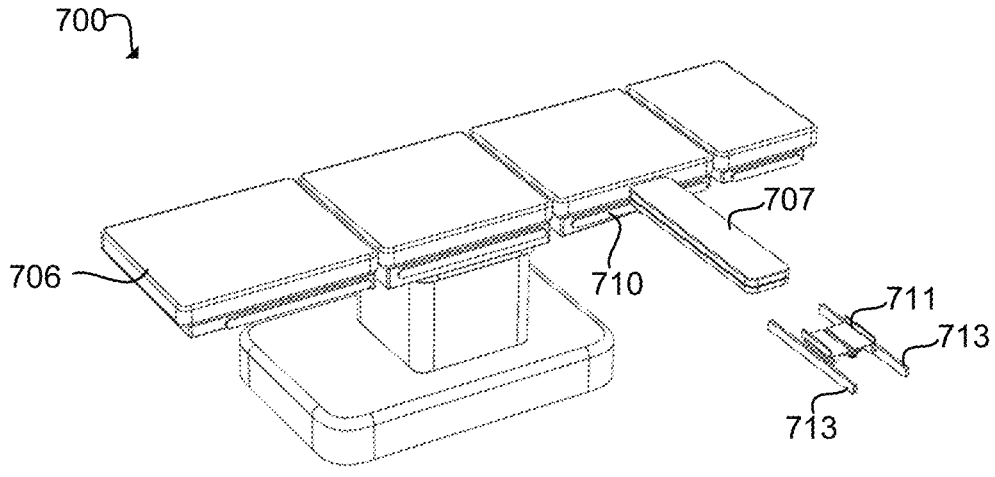
FIG. 9A shows a perspective view of another example surgical table with a surgical arm board and with a rail system detached from the arm board, in accordance with some embodiments of this disclosure.
Figure 9B:
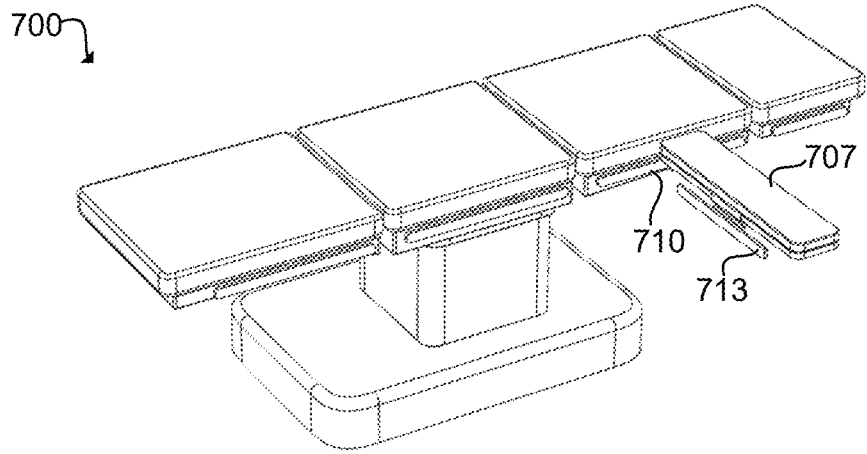
FIG. 9B shows a perspective view of the example surgical table of FIG. 9A with the rail system attached to the arm board, in accordance with some embodiments of this disclosure.
Figure 9C:
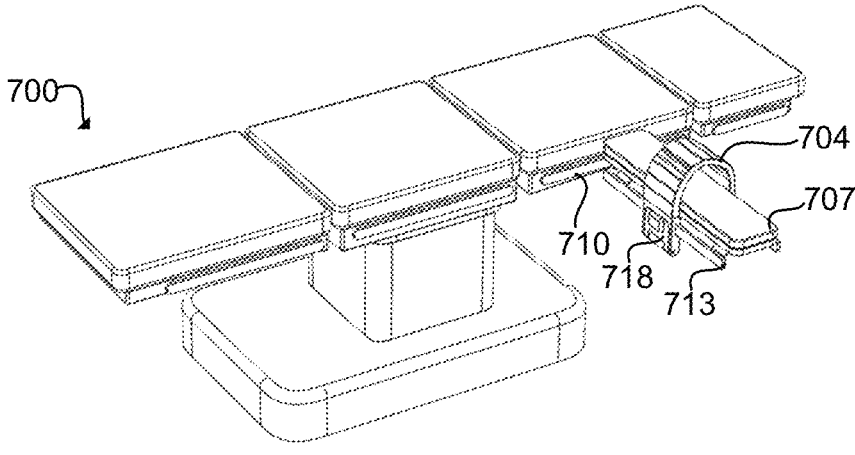
FIG. 9C shows a perspective view of the example surgical table of FIG. 9B with an example adjustable limb restraint connected to the arm board, in accordance with some embodiments of this disclosure.

Referring now to FIGS. 9A-C, some embodiments of a system 700 using one or more adjustable limb restraints 704 can be employed for positioning an arm of a patient on a surgical arm board 707. The surgical table 706 can share features with the surgical table 106. For example, the surgical table 706 can include one or more rails 710 that extend along each side of the surgical table 706, similar to the rails 110 that extend along each side of the surgical table 106. The surgical arm board 707 can connect to one of the rails 710 to secure the surgical arm board 707 to the surgical table 706.

In some embodiments, the surgical arm board 707 can include a rail assembly 711 that is removably attached to the surgical arm board 707. The rail assembly 711 can include arm board rails 713 that, when the rail assembly 711 is attached to the surgical arm board 707, extend along the sides of the surgical arm board 707. In some embodiments, the arm board rails 713 can extend from the surgical arm board 707 in a manner similar to the rails 710 and the surgical table 706.

In the depicted system 700, the one or more adjustable limb restraints 704 can share the features of the adjustable limb restraints 104, 604a, 604b described in detail above, including the linkage assemblies 140, 240 described in detail above. A handle body 718 (similar to body 118) of the adjustable limb restraint 704 can connect to the arm board rails 713 of the surgical arm board 707 to provide releasable engagement with the arm board 707, and the handle body 718 can include a handle actuator (similar to actuator 170) to shift between an unlocked and locked position to thereby releasably lock the linkage assembly in a selected position around the patient's limb. The adjustable limb restraint 704 can extend around a patient's arm and to secure the positioning of the arm on the arm board 707. The adjustable limb restraint 704 can include a padded sleeve (e.g., similar to padded sleeve 130), which is removed from view in FIG. 9C for illustrative purposes.

Figure 10A:
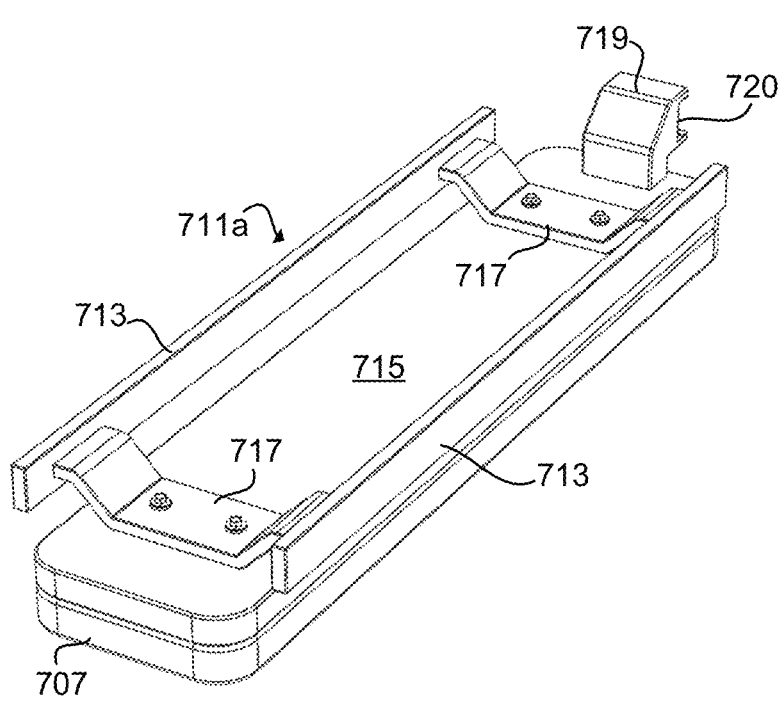
FIG. 10A shows a bottom perspective view of an example arm board, in accordance with some embodiments of this disclosure.

Referring to FIG. 10A, the surgical arm board 707 is illustrated with a rail assembly 711a attached to a bottom surface 715 of the surgical arm board 707. The rail assembly 711a can include brackets 717 that are attached to the bottom surface 715 of the surgical arm board 707. For example, the brackets 717 can be attached via fasteners to the bottom surface 715, the fasteners can extend into the surgical arm board 707 to secure the rail assembly 711a to the surgical arm board 707. The brackets 717 can be spaced apart along the bottom surface 715 of the surgical arm board 707. The brackets 717 can extend downwardly away from the bottom surface 707 and connect to the arm board rails 713. The surgical arm board 707 includes an attachment bracket 719 that defines a mating interface surface 720 that is dimensioned to receive the rail 710 and slidably engage with the rail 710.

Figure 10B:
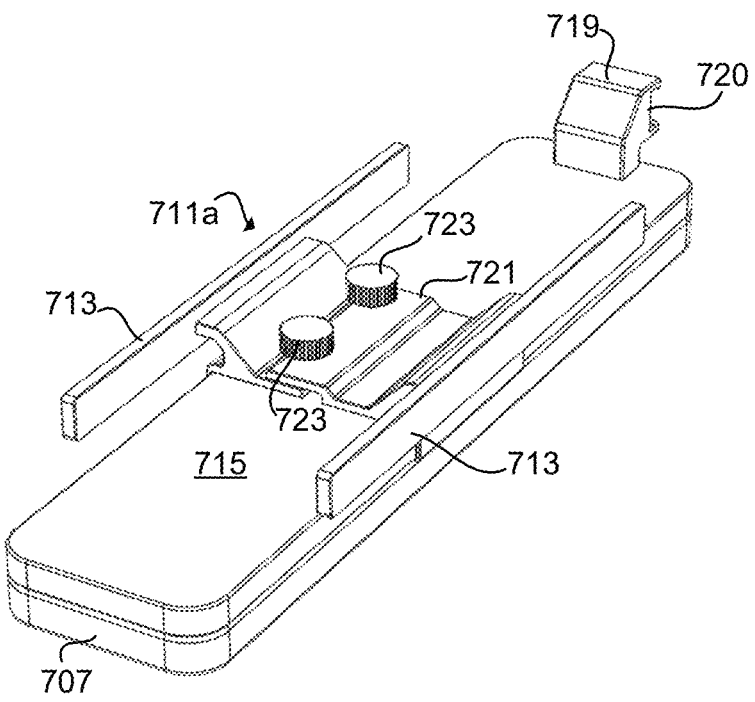
FIG. 10B shows a bottom perspective view of another example arm board, in accordance with some embodiments of this disclosure.

Referring to FIG. 10B, the surgical arm board 707 is illustrated with a rail assembly 711b attached to a bottom surface 715 of the surgical arm board 707. The rail assembly 711b can include a brackets 721 that extends around each side of the bottom surface 715 of the surgical arm board 707. The bracket 721 can be tightened around the surgical arm board 707 (e.g., via tension members 723) to provide a readily removable rail assembly 711b. The bracket 721 can extend downwardly away from the bottom surface 707 and connect to the arm board rails 713. The surgical arm board 707 includes an attachment bracket 719 that defines a mating interface surface 720 that is dimensioned to receive the rail 710 and slidably engage with the rail 710. The rail assembly 711 of FIG. 9C can be rail assembly 711a or 711b of FIGS. 10A-B.

Figure 11A:
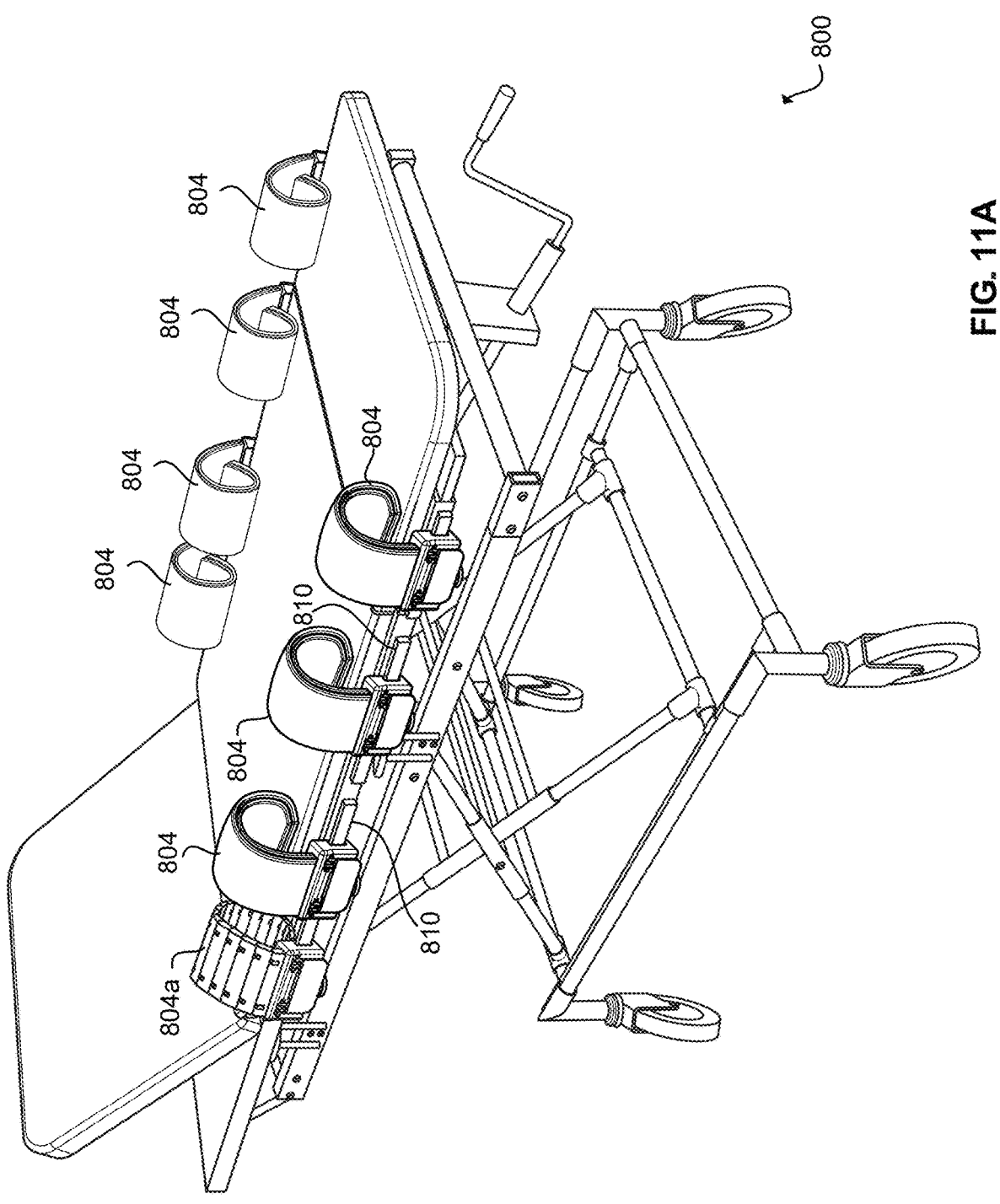
FIG. 11A shows a perspective view of another example system for positioning a patient relative to a medical transport apparatus, in accordance with some embodiments of this disclosure.
Figure 11B:
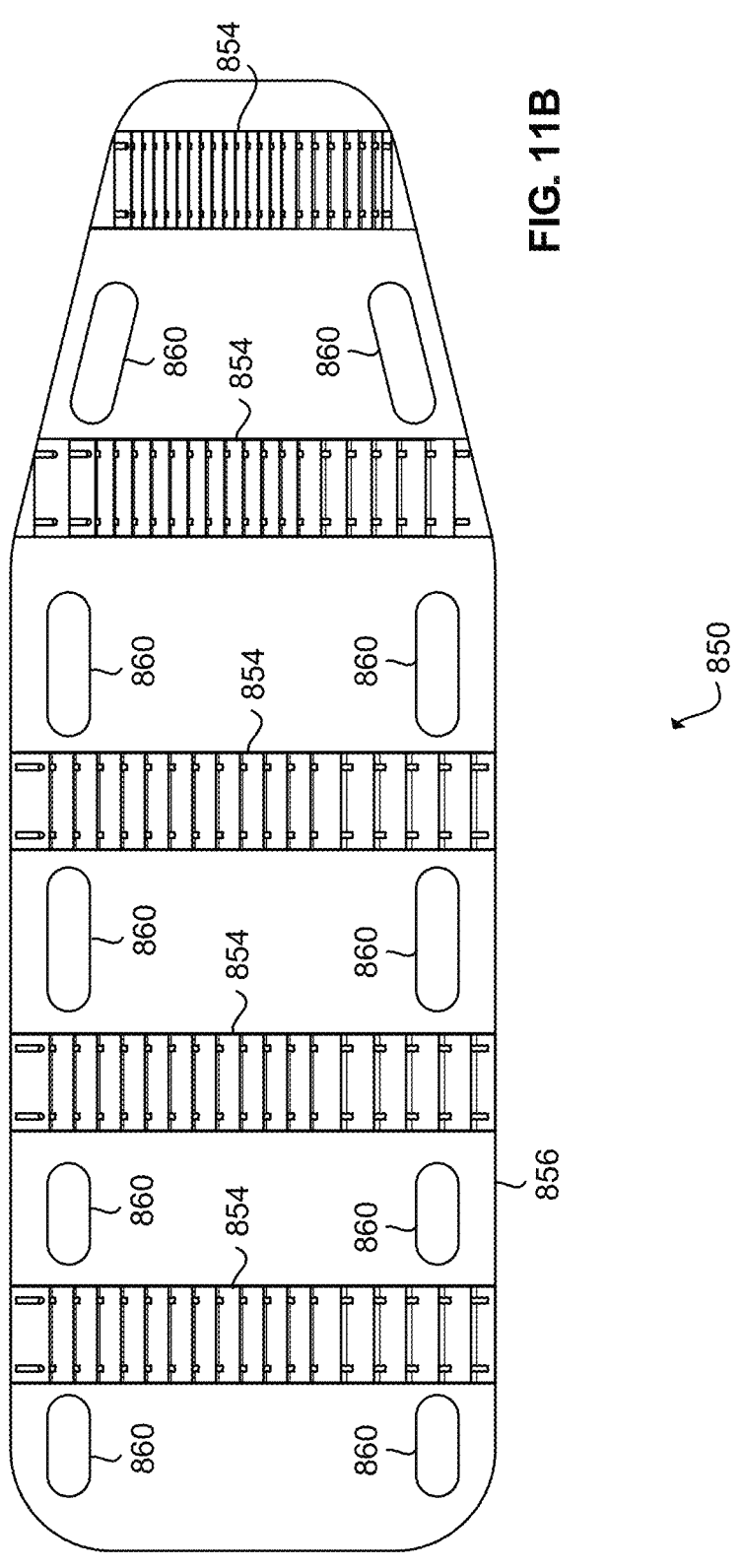
FIG. 11B shows a top view of a further example system for positioning a patient relative to another medical transport apparatus, in accordance with some embodiments of this disclosure.

Referring to FIGS. 11A-B, some embodiments of the adjustable limb restraints can be used in systems 800, 850 to maintain a position of a patient relative to a medical transport apparatus. For example, as shown in FIG. 8A, the system 800 includes a portable stretcher 806 (e.g., for transport in and out of an ambulance vehicle or transport through a medical building) that has one or more adjustable limb restraints 804a and 804 that are connected to one or more rails 810 of the portable stretcher 806. The adjustable limb restraints 804a and 804 can share the features of the adjustable limb restraints 104a, 104, 604a, 604b described in detail above, including the handle body and linkage assembly operable to releasably lock in a customized configuration. The adjustable limb restraints 804 include the protective sleeve (similar to sleeve 130 described above), and the protective sleeve for adjustable limb restraint 804a is removed from view in FIG. 8A for illustrative purposes. In another example, as shown in FIG. 8B, the system 850 includes a stretcher board 856 (e.g., configured to receive a patient for transport via one or more users carrying the stretcher board) that has a set of adjustable limb restraints 854 connected side edges of the portable stretcher 856 (at longitudinal positions) between one or more handles 860. The adjustable limb restraints 854 can share the features of the adjustable limb restraints 104a, 104, 604a, 604b, 804 described in detail above, including the handle body and linkage assembly operable to releasably lock in a customized configuration. The adjustable limb restraints 854 can include a protective sleeve (e.g., similar to protective sleeve 130), which is removed from view in FIG. 8B for illustrative purposes Referring now to FIG. 9, some embodiments of a system 900 for positioning a patient can include one or more adjustable restraint devices 904 that use deformable internal wire structures to retain the customized shape of the cuff body. For example, each restraint system 904 can include deformable metallic wire structures that extend longitudinally within the padded outer body, and the deformable metallic wire structures are plastically deformable by a user so as to curl or bend to a customized configuration that engages with a patient's limb. As such, each adjustable restraint device 904 can be formed into various shapes to hold a patient in position on a surgical table or surgical transport device. Each restraint system 904 can include a padded cover that shares features with the protective sleeve 130 described above. In some aspects, the restraint systems 904 can include a mattress extension 909 that connects the restraint systems 904 together and extends under a mattress resting on a surgical table to connect the restraint systems to an operating table 906.

In some embodiments, the restraint systems described herein can be implemented on a variety of surgical tables for a variety of patients and subjects. While human subjects have been described above, the restraint systems described herein are not limited to use for human subjects. For example, the restraint systems described herein can be implemented in veterinary applications. Veterinary applications can include animals of various shapes and sizes. The restraint systems described herein can facilitate a customizable approach to restraining animals for veterinary procedures.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

Accordingly, other implementations are within the scope of the following claims.

What is claimed is:

1. A flexible cuff system for releasably maintaining a position of a patient, comprising:
  a flexible cuff body adjustable from a first orientation to a user-selected orientation to retain a limb in a selected position relative to a medical support substrate, the flexible cuff body including a series of links that are adjustably connected together via a series of first end connectors of each link body configured to connect to a series of second end connectors of a series of brackets and one or more cables; and
  a handle body connected to a base portion of the flexible cuff body, the handle body including a handle that is movable between a locked position and an unlocked position, and the handle body defining a mating interface surface to slidably engage the medical support substrate;
  wherein, responsive to the handle being moved to the unlocked position, the flexible cuff body is adjustable from the first orientation to the user-selected orientation to extend around the limb,
  wherein, responsive to the handle being moved to the locked position while the flexible cuff body is in the user-selected orientation, the flexible cuff body is locked in the user-selected orientation by compressing the first end connectors and second end connectors together to retain the limb in the selected position relative to the medical support substrate,
  wherein the one or more cables includes a longitudinal cable that extends from the handle body through the series of links of the flexible cuff body that are adjustably connected together and movable to a linked position relative to one another, and
  wherein the handle is connected to the longitudinal cable, and responsive to the handle being moved to the locked position, the handle applies tension to the longitudinal cable to fix the series of links in the linked position relative to one another.

2. The flexible cuff system of claim 1, wherein the series of first end connectors form a beveled spline receiver and the series of second end connectors form a beveled spline.

3. The flexible cuff system of claim 1, wherein each link comprises a transverse cable that connects to the longitudinal cable.

4. The flexible cuff system of claim 1, wherein responsive to the handle being moved to the unlocked position, the series of links are pivotable with respect to each other to adjust an overall shape of the series of links.

5. The flexible cuff system of claim 1, wherein the flexible cuff body extends away from the handle body toward a free end of the flexible cuff body, and the free end of the flexible cuff body includes a fastener configured to connect to a second flexible cuff body.

6. The flexible cuff system of claim 1, wherein the medical support substrate is a surgical table, and the mating interface surface of the handle body configured to slidably engage with a rail of the surgical table.

7. The flexible cuff system of claim 1, wherein the medical support substrate is an arm bar extension of a surgical table, and the mating interface surface of the handle body configured to slidably engage with the arm bar extension of a surgical table.

8. The flexible cuff system of claim 1, the flexible cuff body comprises a fluid impermeable padded outer sleeve having an end opening sized to slidably receive a free end of the series of links of the flexible cuff body into an interior pocket of the fluid impermeable padded sleeve such that the fluid impermeable padded sleeve is slidably mounted over the series of links from the free end of the series of links to the base portion of the flexible cuff body.

9. A system comprising:
  a surgical table including one or more rails that extend along one or more sides of the surgical table;
  a plurality of adjustable limb restraints releasably lockable at selectable positions along the one or more rails of the surgical table, each of the adjustable limb restraints including:
    a flexible cuff body adjustable from a first orientation to a user-selected orientation to retain a limb in a user-selected position relative to the surgical table, the flexible cuff body including a series of links that are adjustably connected together via a series of first end connectors of each link body configured to connect to a series of second end connectors of a series of brackets and one or more cables; and
    a handle body connected to a base of the flexible cuff body and including a handle movable between a locked position and an unlocked position, and the handle body defining a mating interface surface to slidably engage at least one of the one or more rails;
  wherein, responsive to the handle being moved to the unlocked position, the flexible cuff body is adjustable from the first orientation to the user-selected orientation to extend around the limb;
  wherein, responsive to the handle being moved to the locked position while the flexible cuff body is in the user-selected orientation, the flexible cuff body is locked in the user-selected orientation by compressing the first end connectors and second end connectors together to retain the limb in the selected position relative to the surgical table;
  wherein the flexible cuff body includes a longitudinal cable that extends from the handle body through the series of links of the flexible cuff body that are adjustably connected together and movable to a linked position relative to one another;
  wherein responsive to the handle being moved to the unlocked position, the series of links are movable with respect to each other to adjust the flexible cuff body to the user-selected orientation shaped to extend around the limb; and
  wherein, responsive to the handle being moved to the locked position, the series of links are mechanically fixed relative to each other to releasably lock the flexible cuff body in the user-selected orientation.

10. The system of claim 9, wherein, responsive to the handle being moved to the unlocked position, the series of links are pivotable with respect to each other to adjust an overall shape of the flexible cuff body.

11. The system of claim 9, wherein each of the plurality of adjustable limb restraints operate independently from one another.

12. A method of maintaining a position of a patient, the method comprising:

releasably locking a handle body of an adjustable limb restraint to a rail of an operating table at a selected location relative to a limb of a patient on the operating table;

adjusting a flexible cuff body of the adjustable limb restraint to a selected shape to engage with the limb of the patient; and adjusting an actuator on the handle body of the adjustable limb restraint to releasably lock the flexible cuff body in the selected shape by compressing a series of first end connectors and a series of second end connectors of the flexible cuff body together;

wherein in response to said adjusting the actuator on the handle body, a series of links of the flexible cuff body are mechanically fixed relative to each other to releasably lock the flexible cuff body in the selected shape.

13. The method of claim 12, wherein said adjusting the flexible cuff body comprises pivoting the series of links of the flexible cuff body that are adjustably connected to each other and arranged within a padded sleeve of the flexible cuff body.

14. The method of claim 12, wherein the limb of the patient is an arm, leg, or torso of the patient.

<center>*   *   *   *   *</center>